(12) United States Patent
Ortiz et al.

(10) Patent No.: US 7,445,622 B2
(45) Date of Patent: Nov. 4, 2008

(54) ANASTOMOTIC RING APPLIER WITH DOUBLE MOTION ACTUATION

(75) Inventors: Mark S. Ortiz, Milford, OH (US); Eugene L. Timperman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 492 days.

(21) Appl. No.: 11/122,349

(22) Filed: May 5, 2005

(65) Prior Publication Data

US 2006/0253140 A1   Nov. 9, 2006

(51) Int. Cl.
*A61B 17/10* (2006.01)
*A61B 17/08* (2006.01)
(52) U.S. Cl. ...................... 606/139; 606/153
(58) Field of Classification Search ......... 606/139–141; 623/1.11, 1.12; 227/19, 175.1, 178, 31, 179.1; 74/29, 30; *A61B 17/02, 17/03, 17/10, 17/68*
See application file for complete search history.

(56) References Cited

U.S. PATENT DOCUMENTS

| | | | | |
|---|---|---|---|---|
| 5,282,810 | A * | 2/1994 | Allen et al. | 606/150 |
| 5,855,312 | A | 1/1999 | Toledano | |
| 6,171,321 | B1 | 1/2001 | Gifford et al. | |
| 6,428,550 | B1 | 8/2002 | Vargas et al. | |
| 6,451,029 | B1 | 9/2002 | Yeatman | |
| 6,485,496 | B1 | 11/2002 | Suyker et al. | |
| 6,860,895 | B1 * | 3/2005 | Akerfeldt et al. | 606/215 |
| 2003/0032967 | A1 | 2/2003 | Park et al. | |
| 2003/0191482 | A1 | 10/2003 | Suyker et al. | |
| 2005/0143809 | A1 * | 6/2005 | Salahieh et al. | 623/2.11 |

FOREIGN PATENT DOCUMENTS

| | | |
|---|---|---|
| EP | 1520531 | 6/2005 |
| WO | WO 2004/098417 | 11/2004 |

OTHER PUBLICATIONS

Office Action dated Jan. 4, 2006, for U.S. Appl. No. 10/675,497, filed Sep. 30, 2003.
EPO Search Report, 06252365.9, pp. 1-10.

* cited by examiner

*Primary Examiner*—Julian W. Woo
*Assistant Examiner*—Dianne Dornbusch
(74) *Attorney, Agent, or Firm*—Forst Brown Todd LLC

(57) ABSTRACT

A surgical tool for deploying an anastomotic ring comprises a handle and a ring deployment mechanism at the distal end of a shaft. The ring deployment mechanism has a distal portion and a proximal portion, and is moveable from an unactuated position to an actuated position to deploy an anastomotic ring. To prevent tissue from becoming trapped in the deployment mechanism during insertion or extraction of the tool, distal and proximal sheaths are configured to cover distal and proximal portions of the ring deployment mechanism, respectively. An actuation mechanism in the handle permits advancement of the distal sheath and actuation of the distal portion of the ring deployment mechanism with a single movement of a first actuator slider. The actuation mechanism also permits retraction of the proximal sheath and actuation of the proximal portion of the ring deployment mechanism with a single movement of a second actuator slider.

16 Claims, 20 Drawing Sheets

ANASTOMOTIC RING APPLIER WITH DOUBLE MOTION ACTUATION

FIELD OF THE INVENTION

The present invention relates, in general, to surgery and, more particularly, to a device for performing a surgical procedure on the digestive system.

BACKGROUND OF THE INVENTION

The percentage of the world population suffering from morbid obesity is steadily increasing. Severely obese persons may be susceptible to increased risk of heart disease, stroke, diabetes, pulmonary disease, and accidents. Because of the effects of morbid obesity on the life of the patient, methods of treating morbid obesity have been the subject of intense research.

One known method for treating morbid obesity includes the use of anastomotic rings. Devices for applying anastomotic rings are known in the art. Devices of this nature are commonly adapted to insert a compressed anastomotic ring to an anastomotic opening formed between proximate gastrointestinal tissue walls. These applier devices may utilize a ring deployment mechanism comprising an expansion element that is actuated once the compressed ring is placed in the anastomotic opening, causing the anastomotic ring to expand from its compressed, cylindrically-shaped position to an actuated, hollow rivet-shaped position.

With some conventional anastomotic ring applier devices that use fingers or similar members to expand anastomotic rings, it may be possible for tissue to be trapped between the fingers of the applier device when it is inserted adjacent the proximate gastrointestinal tissue walls. Similarly, it may be possible for tissue to become trapped in the deployment mechanism during extraction of the device from the anastomosis site. The trapping of tissue between the fingers may result in undesirable consequences, such as pinching or tearing of the tissue, or even a compromise in the integrity of the anastomosis.

Some anastomotic ring applier devices known in the art incorporate a tubular sheath that is slideably located on the elongated shaft. The tubular sheath is typically in position over the ring deployment mechanism while the device is inserted adjacent the anastomosis site and during extraction of the device, and may be retracted to allow deployment of the ring. However, separate mechanisms are typically used to effect retraction of the sheath and actuation of the ring deployment mechanisms. Thus, it may be desirable to have an anastomotic ring applier device that provides a reduced likelihood of tissue becoming trapped in the ring deployment mechanism of the device, yet does not necessarily require additional steps to effect sheath retraction.

BRIEF SUMMARY OF EMBODIMENTS OF THE INVENTION

In one embodiment, a surgical instrument for implanting an anastomotic ring device comprises a ring deployment mechanism. The ring deployment mechanism is configured to receive an anastomotic ring, and is operable to move between an unactuated position and an actuated position. The instrument further comprises a shaft in communication with the ring deployment mechanism. The shaft comprises one or more transfer members operatively configured to transfer actuating forces to the ring deployment mechanism, The shaft further comprises a sheath device operable to selectively move from a first configuration to a second configuration. The sheath device is configured to cover at least a portion of the ring deployment mechanism when the sheath is in the first configuration. The sheath device is configured to uncover the at least a portion of the ring deployment mechanism when the sheath device is moved to the second configuration. The instrument further comprises an actuation mechanism operable to perform acts of actuating at least a portion of the ring deployment mechanism and moving at least a portion of the sheath device to the second configuration substantially contemporaneously.

In another embodiment, a surgical instrument for deploying an anastomotic ring device comprises a ring deployment mechanism. The ring deployment mechanism is configured to deploy an anastomotic ring, and is operable to move between an unactuated position and an actuated position. The ring deployment mechanism comprises a proximal portion and a distal portion. The instrument further comprises a shaft in communication with the ring deployment mechanism. The shaft comprises one or more transfer members operatively configured to transfer actuating forces to the ring deployment mechanism. The shaft further comprises a proximal sheath configured to cover the proximal portion of the ring deployment mechanism when the proximal sheath is in a first configuration. The proximal sheath is configured to uncover at least a portion of the proximal portion of the ring deployment mechanism when the proximal sheath is moved proximally from the first configuration. The shaft further comprises a distal sheath configured to cover the distal portion of the ring deployment mechanism when the distal sheath is in a second configuration. The distal sheath is configured to uncover at least a portion of the distal portion of the ring deployment mechanism when the distal sheath is moved distally from the second configuration. The instrument further comprises an actuation mechanism. The actuation mechanism comprises a first member operable to actuate the proximal portion of the ring deployment mechanism and move the proximal sheath proximally contemporaneously. The actuation mechanism further comprises a second member operable to actuate the distal portion of the ring deployment mechanism and move the distal sheath distally contemporaneously.

In yet another embodiment, a surgical instrument for deploying an anastomotic ring device comprises a ring deployment mechanism configured to deploy an anastomotic ring device. The ring deployment mechanism comprises a set of proximal fingers and a set of distal fingers. The proximal fingers are configured to actuate in response to a first distal force. The distal fingers are configured to actuate in response to a first proximal force. The instrument further comprises a proximal sheath configured to cover the proximal fingers. The proximal sheath is operable to uncover the proximal fingers in response to a second proximal force. The instrument further comprises a distal sheath configured to cover the distal fingers. The distal sheath is operable to uncover the distal fingers in response to a second distal force. The instrument further comprises an actuation mechanism. The actuation mechanism comprises a first member operable to communicate the first distal force and the second proximal force contemporaneously. The actuation mechanism further comprises as second member operable to communicate the first proximal force and the second distal force contemporaneously.

These and other embodiments will be described in greater detail below. In addition, alternate embodiments will become apparent to those of ordinary skill in the art.

BRIEF DESCRIPTION OF THE FIGURES

The accompanying drawings, which are incorporated in and constitute a part of this specification, illustrate versions of the invention, and, together with the general description of the invention given above, and the detailed description of the versions given below, serve to explain the principles of the present invention.

DETAILED DESCRIPTION OF EMBODIMENTS OF THE INVENTION

Figure 1:
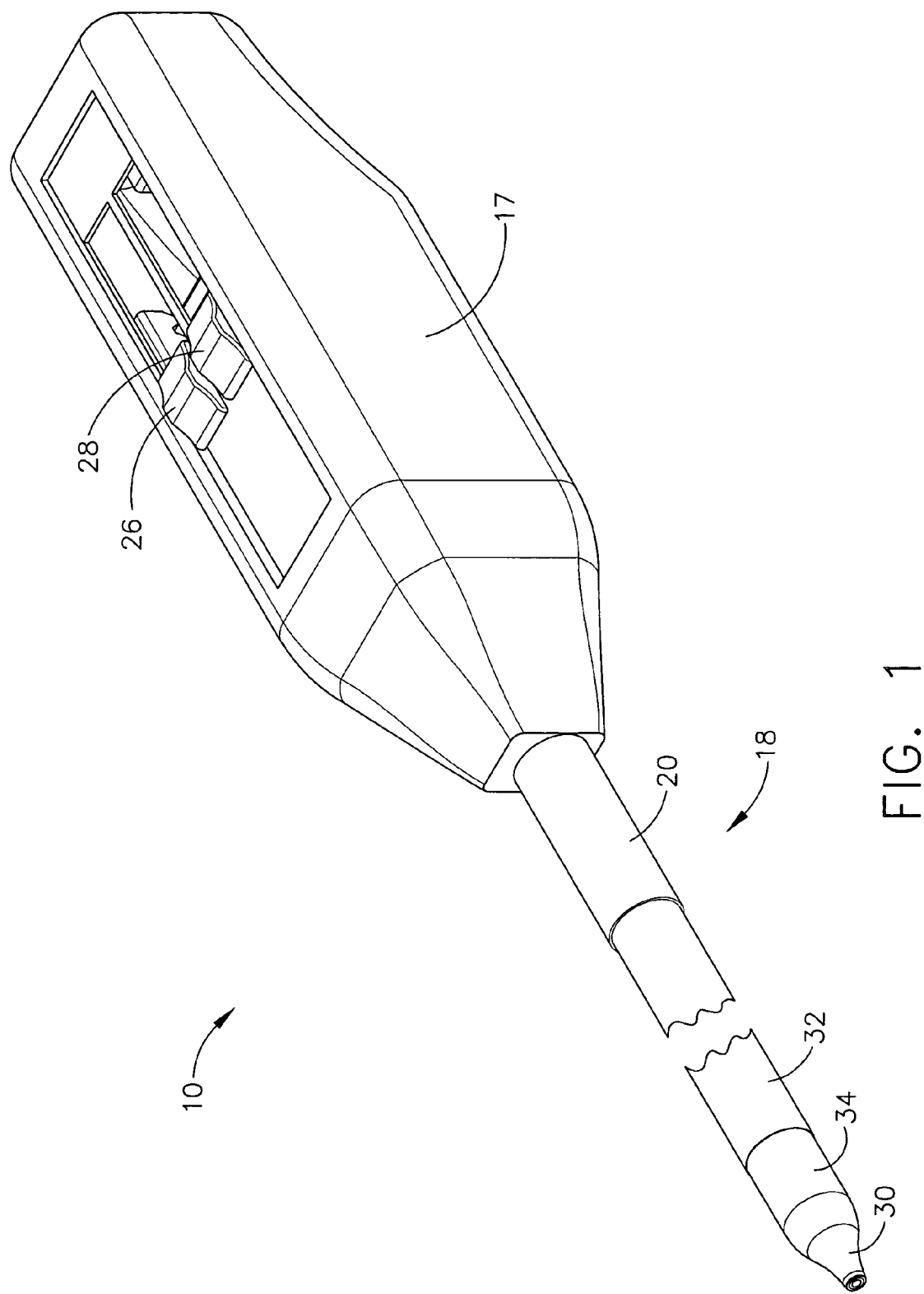
FIG. 1 is a perspective view of an anastomotic ring applier device.
Figure 2:
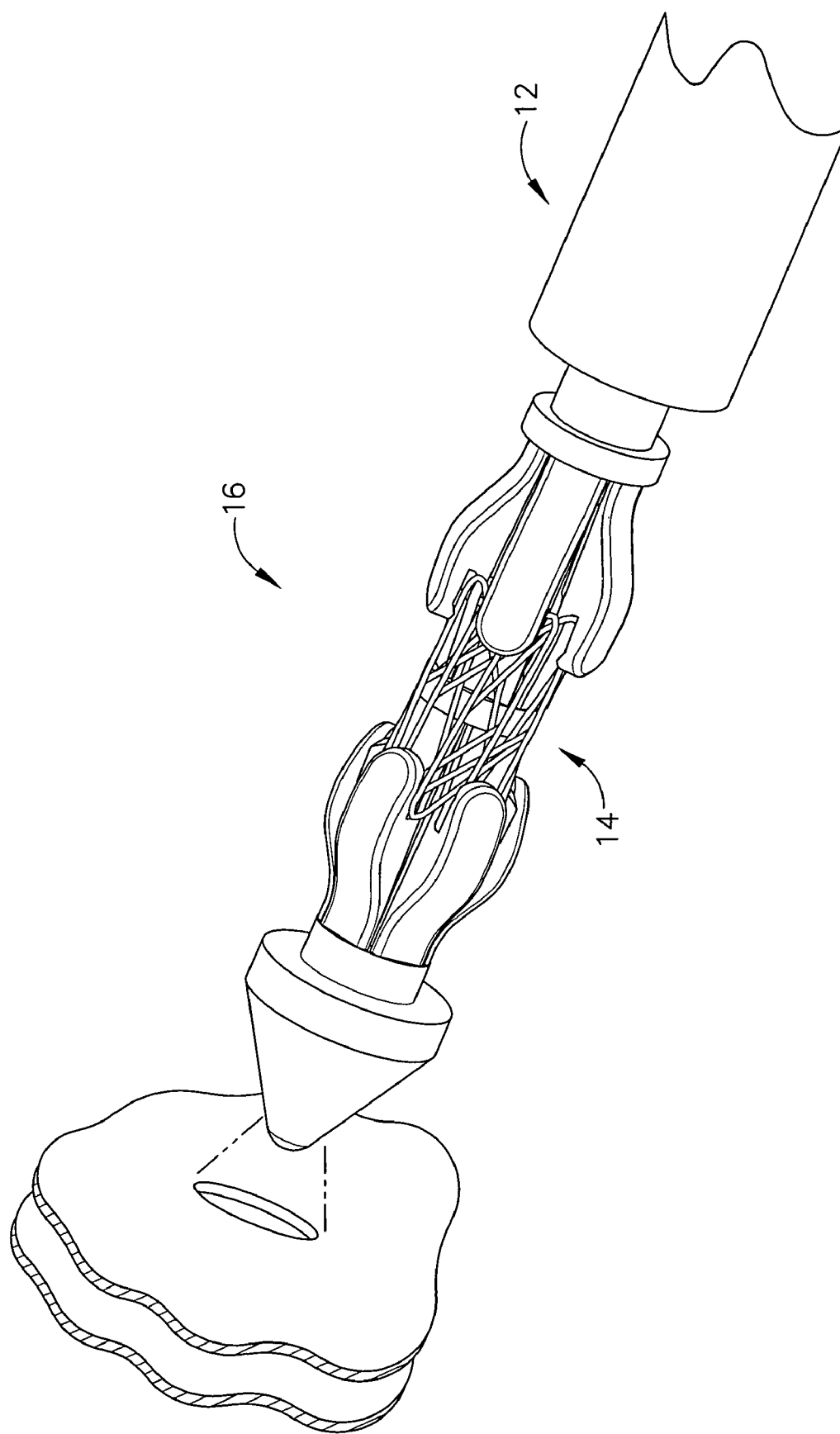
FIG. 2 is a partial perspective view of the distal portion of an anastomotic ring applier device holding an anastomotic ring in an unactuated position.
Figure 3:
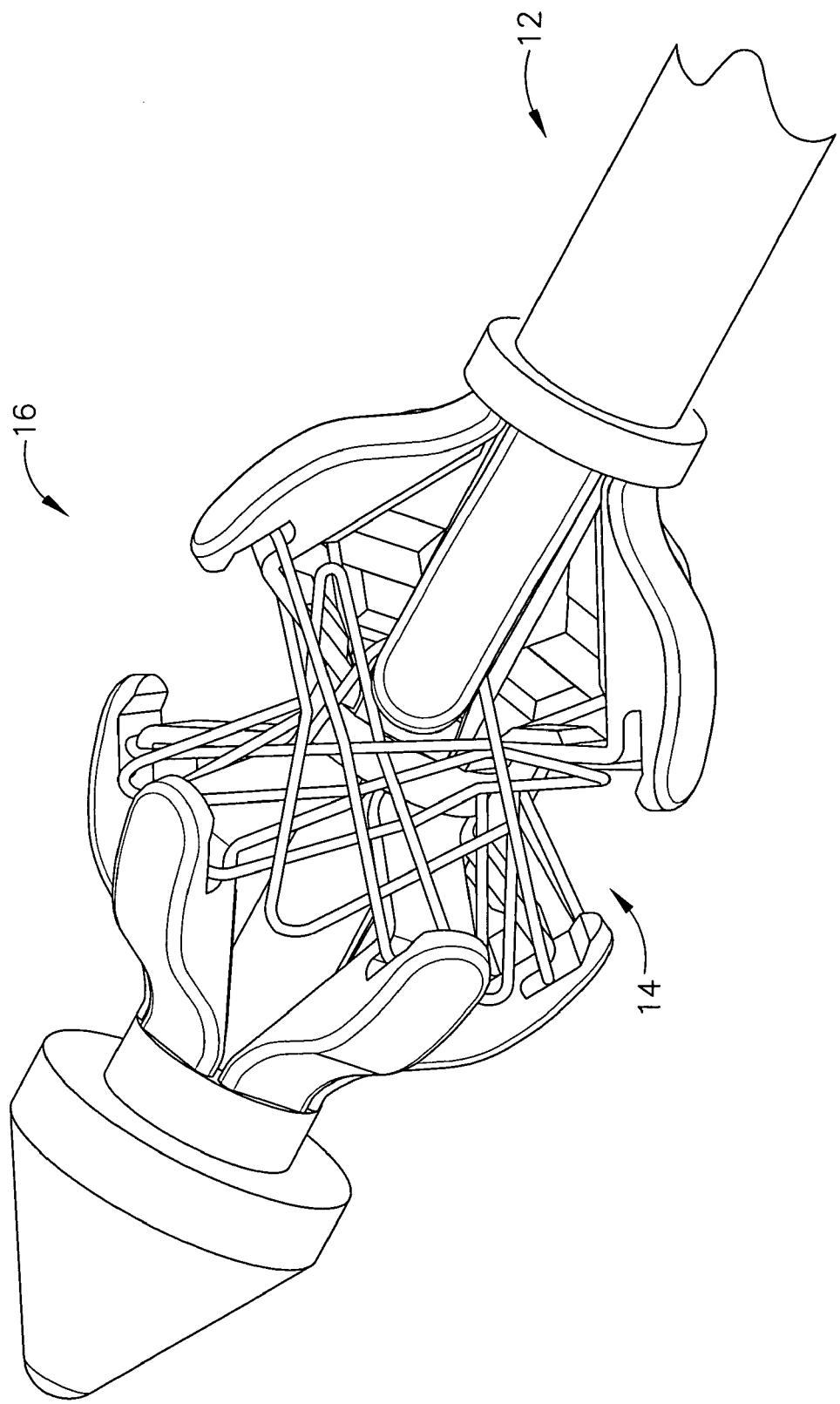
FIG. 3 is a partial perspective view of the distal portion of the device of FIG. 2 shown without a sheath holding an anastomotic ring in the actuated position.
Figure 4:
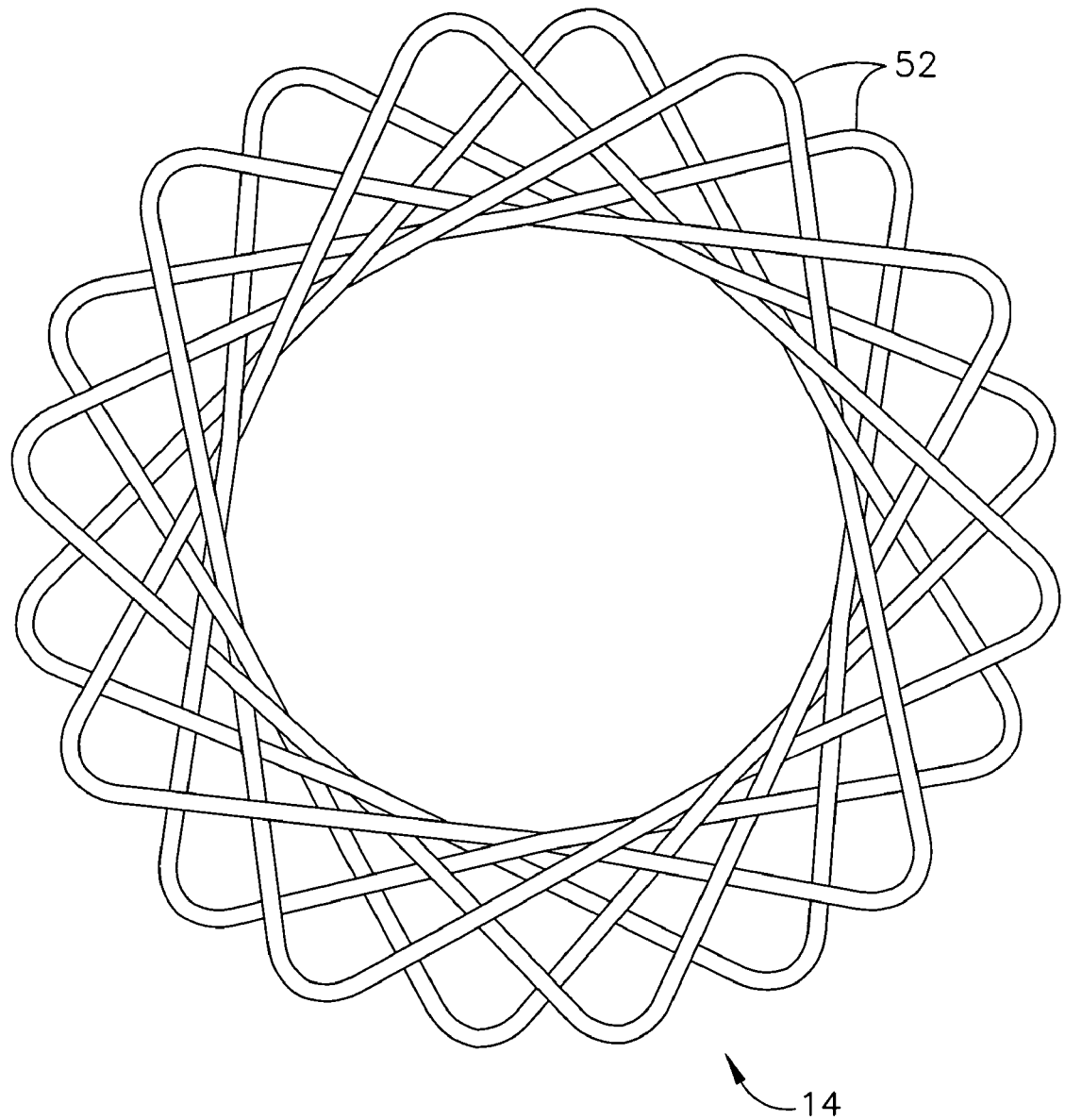
FIG. 4 is a frontal view of an actuated anastomotic ring.

Turning to the Drawings, wherein like numerals denote like components throughout the several views, FIG. 1 depicts an applier 10 that is operable to deploy and actuate an anastomotic ring device (not pictured in FIG. 1) from a generally cylindrical shape to one having properties of a hollow rivet, or ring, capable of forming an anastomotic attachment at an anastomosis target site, such as in a bariatric gastric bypass of a morbidly obese patient. FIG. 2 depicts another applier 12. It will be appreciated that appliers 10, 12 may be used in a variety of ways, including but not limited to laparoscopically or endoscopically. Applier 12 is shown in FIG. 2 with an anastomotic ring 14 on a deployment mechanism 16. In FIG. 2, anastomotic ring 14 is shown in the compressed, cylindrically-shaped position. In FIG. 3, deployment mechanism 16 of applier 12 has moved anastomotic ring 14 to the actuated, hollow rivet-shaped position. FIG. 4 is a close-up view of anastomotic ring 14 in the actuated position. Anastomotic ring 14 may comprise a shape memory effect (SME) material, such as nitinol by way of example only, that further assists in actuation to an engaging hollow rivet shape. Other suitable anastomotic ring 14 materials will be apparent to those of ordinary skill in the art. An exemplary anastomotic ring 14 is described in detail in U.S. Patent Application Publ. No. US 2003/0032967 to Park et al.

It will be appreciated that the terms "proximal" and "distal" are used herein with reference to a clinician gripping a handle of applier 10. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure or other procedures. Use herein of one of these or similar terms should not be construed to limit the present invention for use in only one category of surgical procedure.

Referring to FIGS. 1 and 5-8, applier 10 of the present example comprises a handle 17 connected to the proximal end of an elongated shaft 18. As shown in FIG. 1, elongated shaft 18 is substantially rigid. Of course, shaft 18 may alternatively be flexible (e.g., along its entire length or at one or more joints), resilient, malleable, or have other properties. A ring deployment mechanism 24 is located at the distal end 22 of shaft 18, proximal to a tip 30. As shown in FIG. 1, handle 17 comprises right actuator slider 26 and left actuator slider 28, which are operable to actuate deployment mechanism 24. The functioning of exemplary actuator sliders 26, 28 will be described below. It will be appreciated, however, that actuator sliders 26, 28 may take a variety of other forms and have a variety of other functions.

As shown in FIGS. 5-9 and 12-18, ring deployment mechanism 24 of the present example comprises a plurality of proximal fingers 36, a plurality of distal fingers 38. Proximal fingers 36 are joined by a proximal ring 40, while distal fingers 38 are joined by a distal ring 42. Ring deployment mechanism 24 further comprises a mid-ring 46, which is located between proximal fingers 36 and distal fingers 38. Proximal fingers 36 and distal fingers 38 are each in a double-hinged relationship with mid-ring 46 of ring deployment mechanism 24. Thus, actuation of proximal fingers 36 may be effected by moving proximal fingers 36 distally (i.e. toward mid-ring 46). Similarly, actuation of distal fingers 38 may be effected by moving distal fingers 38 proximally (i.e. toward mid-ring 46). Fingers 36, 38 are configured to hold an anastomotic ring 14 by engaging petals 52 prior to and during deployment of the anastomotic ring 14, and release petals 52 upon deployment of the anastomotic ring 14. Deployment of anastomotic ring 14 may be effected through actuation of fingers 36, 38. Other suitable configurations for ring deployment mechanism 24 will be apparent to those of ordinary skill in the art.

Shaft 18 of the present example comprises a series of concentric tubes. Shaft 18 comprises a tube guide 20, which extends from handle 17 and is integrally formed therewith. Shaft 18 further comprises a proximal sheath 32, which extends through tube guide 20 into handle 17. Proximal sheath 32 is configured to fit over and enclose proximal fingers 36, and may be moved longitudinally to cover and uncover proximal fingers 36. Shaft 18 further comprises an outer tube 43, which extends through proximal sheath 32 into handle 17. Outer tube 43 is fixedly secured to proximal ring 40, and is configured to communicate longitudinal movement to proximal ring 40. Shaft 18 further comprises ground tube 45, which extends through outer tube 43 into handle 17. Ground tube 45 is fixedly secured to mid-ring 46, and is anchored within handle 17 as will be described below. Shaft 18 further comprises inner tube 44, which extends through ground tube 45 into handle 17. Inner tube 44 is fixedly secured to distal ring 42, and is configured to communicate longitudinal movement to distal ring 42. Shaft 18 further comprises tip tube 47, which extends through inner tube 44 into handle 17. Tip tube 47 is fixedly secured to tip 30, and is configured to communicate longitudinal movement to tip 30. Those of ordinary skill in the art will appreciate that any one of tubes 43, 45, 44, 47 may be altered or substituted with any suitable alternative structure, including but not limited to cables.

As shown, a distal sheath 34 extends proximally from tip 30, and is integrally formed therewith. Similar to proximal sheath 32, distal sheath 34 is configured to fit over and enclose distal fingers 38, and may be moved longitudinally to cover and uncover distal fingers 38. It will be appreciated that distal sheath 34 and proximal sheath 34 may serve to prevent tissue from becoming trapped in deployment mechanism 24 when applier 10 is inserted or extracted from an anastomosis site. In another embodiment, a single sheath is used to serve the same purposes as proximal sheath 32 and distal sheath 34 combined. Alternatively, any other structure may be used to serve the same or similar purposes. In addition, it will be appreciated that sheaths 32, 34 or their alternatives may serve a variety of other purposes.

FIGS. 10-20 show exemplary components of handle 17. As shown, the right actuator slider 26 is located in the right half of handle 17, while the left actuator slider 28 is located in the left half of handle 17. While sliders 26, 28 are used in the present example, it will be appreciated that a variety of alternative structures or devices may be used to substitute or supplement sliders 26, 28. In the present example, right actuator slider 26 is integral with a right rack 60 having a plurality of right rack teeth 62. Left actuator slider 28 is integral with a left rack 80 having a plurality of left rack teeth 82. Handle 17 further comprises a right pinion 64 and a left pinion 84. Right pinion 64 comprises a plurality of right pinion teeth 66, a first pin 68, and a second pin 70. First and second pins 68, 70 extend perpendicularly from the face of right pinion 64 (i.e. parallel to the axis of right pinion 64) toward the left side of handle 17. Right pinion teeth 66 are configured to mesh with right rack teeth 62, such that longitudinal motion of right rack 60 will effect rotation of right pinion 64. Left pinion 84 comprises a plurality of left pinion teeth 86, a third pin 88, and a fourth pin 90. Third and fourth pins 88, 90 extend perpendicularly from the face of left pinion 84 (i.e. parallel to the axis of left pinion 84) toward the right side of handle 17. Left pinion teeth 86 are configured to mesh with left rack teeth 82, such that longitudinal motion of left rack 80 will effect rotation of left pinion 84. It will be appreciated that any suitable alternative or supplement to racks 60, 80; pinions 64, 84; and/or pins 68, 70, 88, 90 may be used.

Handle 17 of the present example further comprises first actuator 72, second actuator 76, third actuator 92, and fourth actuator 96. First actuator 72 has upwardly-oriented first slot 74; while second actuator 76 has downwardly-oriented second slot 78. Similarly, third actuator 92 has upwardly-oriented third slot 94; while fourth actuator 96 has downwardly-oriented fourth slot 98. First slot 74 is configured to receive first pin 68; second slot 78 is configured to receive second pin 70; third slot 94 is configured to receive third pin 88; and fourth slot 98 is configured to receive fourth pin 90. Of course, slots 74, 78, 94, 98 may be substituted with any alternative structure or device, as may actuators 72, 76, 92, 96.

Figure 13:
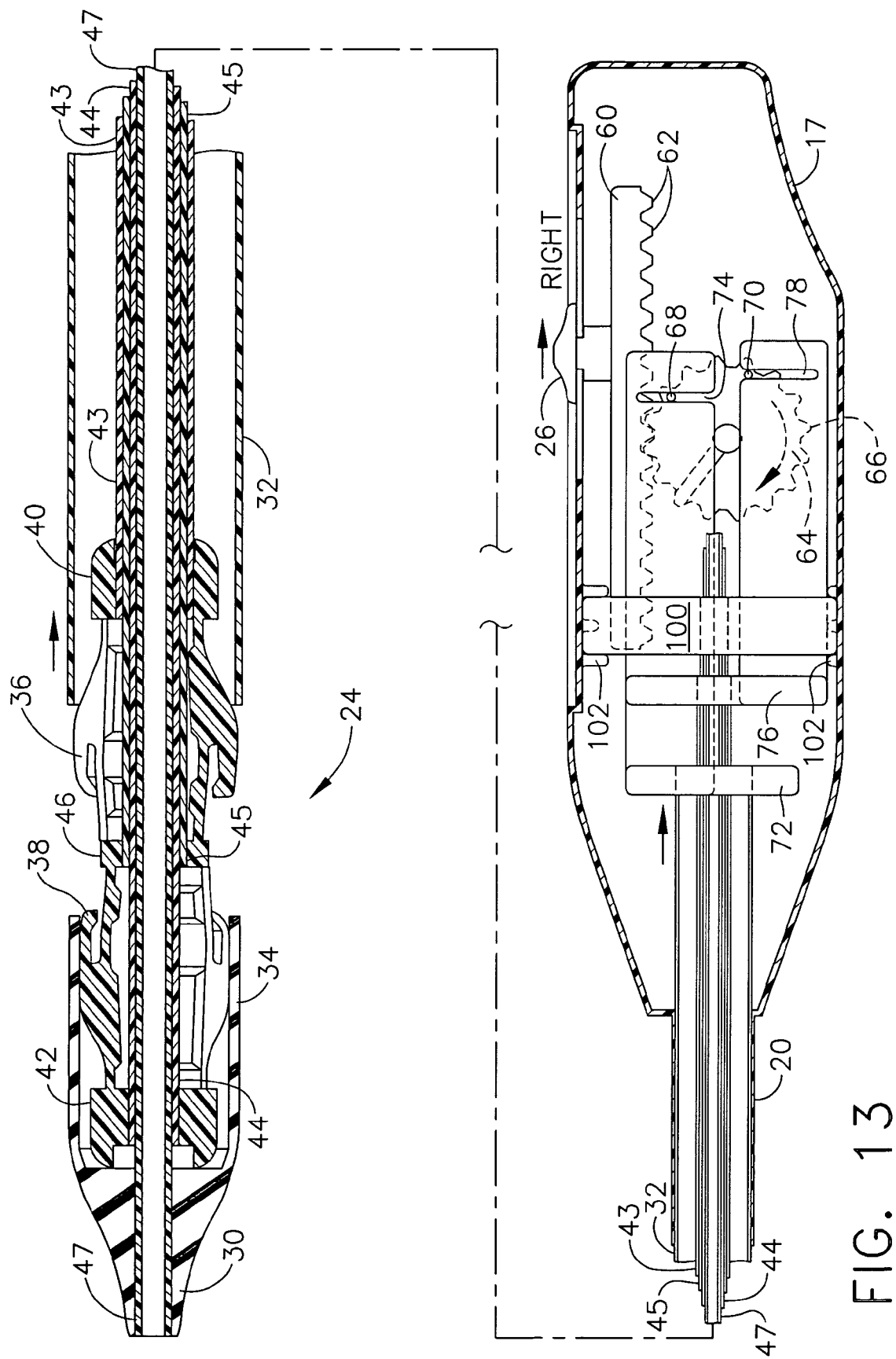
FIG. 13 is a partial cross-sectional view of the distal portion and the right handle portion of the device of FIG. 1, shown with the proximal portion of the sheath partially retracted.

In the present example, first actuator 72 is fixedly secured to proximal sheath 32. Therefore, longitudinal movement of first actuator 72 will effect longitudinal movement of proximal sheath 32. As shown, first slot 74 and first pin 68 are configured to engage such that longitudinal movement of first actuator 72 may be effected by rotation of right pinion 64. Again, rotation of right pinion 64 may be effected by longitudinal movement of right rack 60, such as by actuation of right actuator slider 26. Accordingly, as depicted in FIG. 13, proximal motion of right actuator slider 26 may cause corresponding proximal motion of proximal sheath 32.

Figure 14:
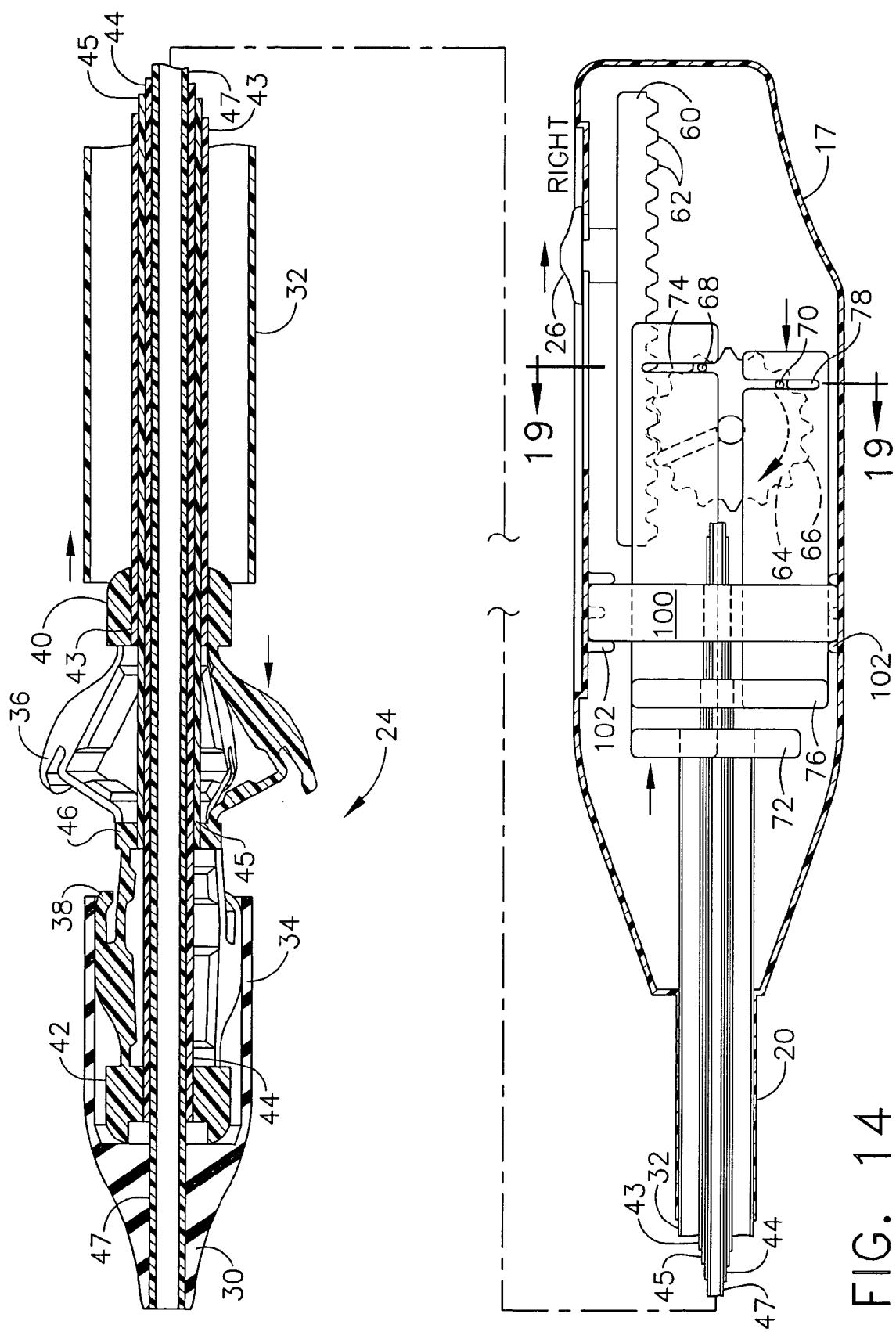
FIG. 14 is a partial cross-sectional view of the distal portion and the right handle portion of the device of FIG. 1, shown with proximal portion of the sheath partially retracted and the proximal portion of the ring deployment mechanism partially actuated.

Second actuator 76 is fixedly secured to outer tube 43, which is also fixedly secured to proximal ring 40 of ring deployment mechanism 24. Thus, longitudinal movement of second actuator 76 will effect longitudinal movement of outer tube 43 and proximal ring 40. As shown, second slot 78 and second pin 70 are configured to engage such that longitudinal movement of second actuator 76 may be effected by rotation of right pinion 64. Again, rotation of right pinion 64 may be effected by longitudinal movement of right rack 60, such as by actuation of right actuator slider 26. Accordingly, as depicted in FIG. 14, proximal motion of right actuator slider 26 may cause corresponding distal motion of proximal ring 40. As discussed above, distal motion of proximal ring 40 of the present example causes actuation of proximal fingers 36.

The proximal end of ground tube 45 is fixedly secured to anchor member 100. Anchor member 100 is held within handle 17 by a plurality of bosses 102, such that longitudinal movement of anchor member 100 relative to handle 17 is prevented. Accordingly, bosses 102, anchor member 100, and ground tube 45 prevent longitudinal movement of mid-ring 46 relative to handle 17.

In light of the foregoing, those of ordinary skill in the art will appreciate that proximal movement of proximal sheath 32 and distal movement of proximal ring 40 may be accomplished in a single motion of right actuator slider 26. In other words, and as shown in FIGS. 5, 6, 8, 13, 14, and 17, proximal fingers 36 of ring deployment mechanism 24 may be revealed (i.e., uncovered by proximal sheath 32) and actuated with a single (e.g., continuous) proximal motion of right actuator slider 26. Of course, applier 10 may be configured such that the same results may be obtained by distal motion of right actuator slider 26. Still other variations will be apparent to those of ordinary skill in the art.

It may be desirable to have some delay between the time that proximal sheath 32 begins retracting and the time that proximal fingers 36 begin actuating. In other words, it may be desirable for the initiation of proximal sheath 32 retraction and proximal finger 36 actuation to be sequential. Such initiation delay may be provided to ensure that proximal sheath 32 does not present an obstacle to or otherwise interfere with actuation of proximal fingers 36. Such delay may be provided by, inter alia, the configuration of right pinion 64, first and second pins 68, 70, and/or first and second actuators 72, 76. An exemplary delay is shown in the series represented by FIGS. 5 and 6, as well as the series represented by FIGS. 13 and 14. Alternatively, in another embodiment of sequential initiation, right pinion 64, first and second pins 68, 70, and/or first and second actuators 72, 76 may be configured such that actuation of proximal fingers 36 does not begin until proximal sheath 32 is fully retracted. In yet another alternate embodiment of sequential initiation, actuation of proximal fingers 36 is initiated before retraction of proximal sheath 32 is initiated. It will be appreciated that, in any of the foregoing embodiments, the delay may be effected even with a single, continuous (i.e. uninterrupted) motion of right actuator slider 26. Still other ways in which a delay may be achieved or embodied will be apparent to those of ordinary skill in the art. Alternatively, it will be appreciated that other configurations exist where a delay is not necessary or otherwise desirable.

Regardless of whether there is a delay between the initiation of proximal sheath 32 retraction and proximal finger 36 actuation (e.g., delay experienced with sequential retraction and actuation), those of ordinary skilled in the art will appreciate that retraction of proximal sheath 32 and actuation of proximal fingers 36 may be effected, at least in part, contemporaneously. In other words, at least a portion of the act of retracting proximal sheath 32 may be performed contemporaneously with at least a portion of the act of actuating proximal fingers 36. Thus, as the term is used herein, "contemporaneously" should not be read to require that these two acts begin and/or end at the same time, although it would include a configuration where the two acts begin and/or end at the same time. "Contemporaneously" would include any configuration where there is at least some temporal overlap between the acts of retracting proximal sheath 32 and actuating proximal fingers 36. "Partially contemporaneously" would include any configuration where the acts of retracting proximal sheath 32 and actuating proximal fingers 36 have temporal overlap, but begin and/or end at different times. As used herein, the term "sequential" and its variants should be read to include configurations where the acts of retracting proximal sheath 32 and actuating proximal fingers 36 begin and/or end at different times. Of course, applier 10 may be configured such that the acts may be performed both contemporaneously and sequentially with the same applier 10 (e.g., the acts begin at different times yet there is temporal overlap in their performance). Any of the foregoing results may be obtained with a single, continuous motion of right actuator slider 26. While such may be provided by the applier 10 of the present example, it will be appreciated that, in actual use, motion of right actuator slider 26 need not in fact be a single, continuous motion.

Figure 15:
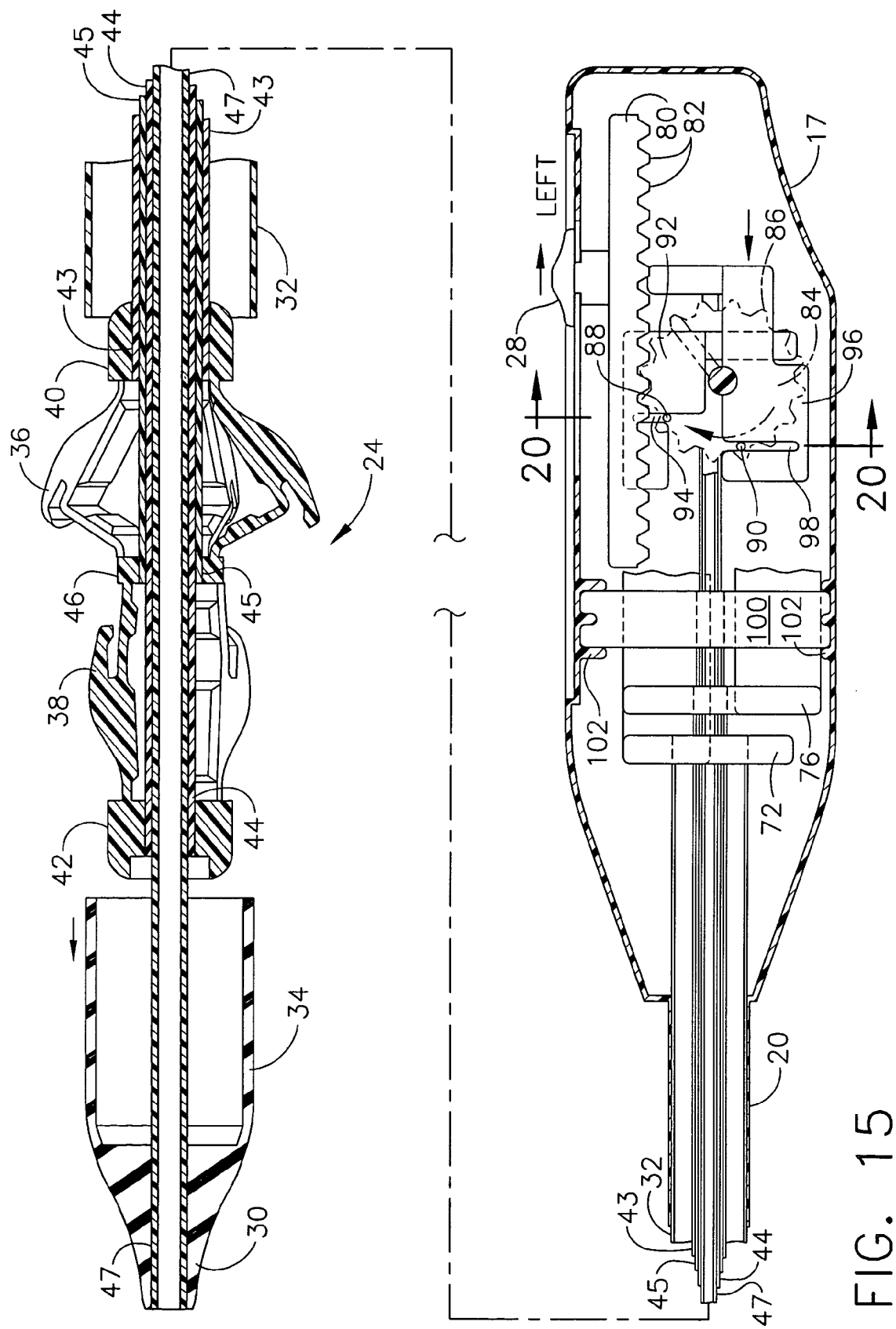
FIG. 15 is a partial cross-sectional view of the distal portion and the left handle portion of the device of FIG. 1, shown with the distal portion of the sheath partially extended.

In the present example, fourth actuator 96 is fixedly secured to tip tube 47, which is also fixedly secured to tip 30. Again, distal sheath 34 is integrally formed with tip 30. Thus, longitudinal movement of fourth actuator 96 will effect longitudinal movement of tip tube 47, tip 30, and distal sheath 34. As shown, fourth slot 98 and fourth pin 90 are configured to engage such that longitudinal movement of fourth actuator 96 may be effected by rotation of left pinion 84. Again, rotation of left pinion 84 may be effected by longitudinal movement of left rack 80, such as by actuation of left actuator slider 28. Accordingly, as depicted in FIG. 15, proximal motion of left actuator slider 28 may cause corresponding distal motion of distal sheath 34.

Figure 16:
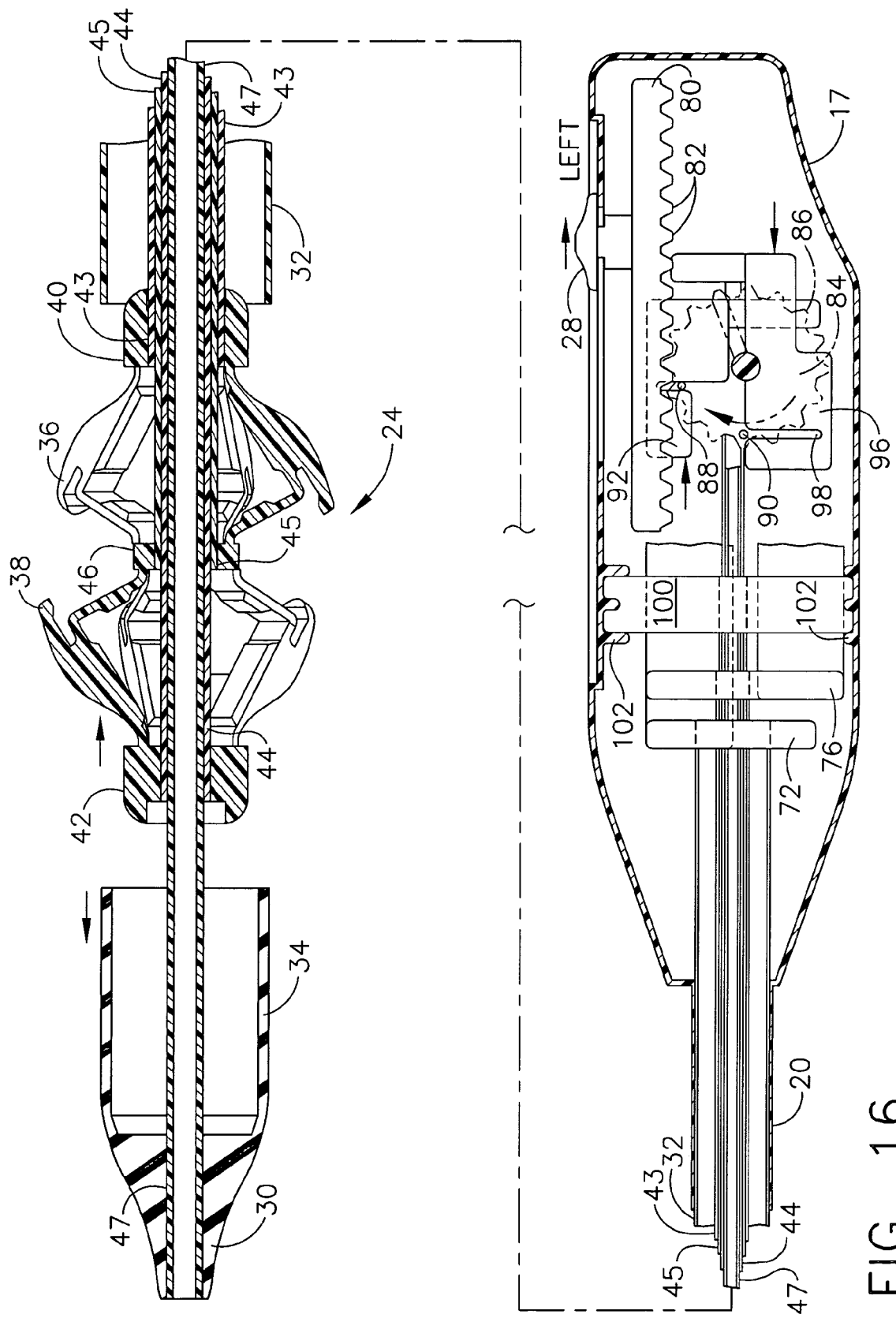
FIG. 16 is a partial cross-sectional view of the distal portion and the left handle portion of the device of FIG. 1, shown with the distal portion of the sheath partially extended and the distal portion of the ring deployment mechanism partially actuated.

Third actuator 92 is fixedly secured to inner tube 44, which is also fixedly secured to distal ring 42 of ring deployment mechanism 24. Therefore, longitudinal movement of third actuator 92 will effect longitudinal movement of inner tube 44 and distal ring 42. As shown, third slot 94 and third pin 88 are configured to engage such that longitudinal movement of third actuator 92 may be effected by rotation of left pinion 84. Again, rotation of left pinion 84 may be effected by longitudinal movement of left rack 80, such as by actuation of left actuator slider 28. Accordingly, as depicted in FIG. 16, proximal motion of left actuator slider 28 may cause corresponding proximal motion of distal ring 42. As discussed above, proximal motion of distal ring 42 of the present example causes actuation of distal fingers 38.

In a manner similar to that encountered in the right half of handle 17, those of ordinary skill in the art will appreciate that distal movement of distal sheath 34 and proximal movement of distal ring 42 may be accomplished in a single motion of left actuator slider 28. In other words, and as shown in FIGS. 5, 7, 8, 15, 16, and 18, distal fingers 38 of ring deployment mechanism 24 may be revealed (i.e. uncovered by distal sheath 34) and actuated with a single (e.g., continuous) proximal motion of left actuator slider 28. Of course, applier 10 may be configured such that the same results may be obtained by distal motion of left actuator slider 28. Still other variations will be apparent to those of ordinary skill in the art.

In addition, as with proximal sheath 32 and proximal fingers 36, it may be desirable to have some delay between the time that distal sheath 34 begins extending distally and the time distal fingers 38 begin actuating. In other words, it may be desirable for the initiation of distal sheath 34 extension and distal finger 38 actuation to be sequential. Such initiation delay may be provided to ensure that distal sheath 34 does not present an obstacle to or otherwise interfere with actuation of distal fingers 38. Such delay may be provided by, inter alia, the configuration of left pinion 84, third and fourth pins 88, 90, and/or third and fourth actuators 92, 96. An exemplary delay is shown in the series represented by FIGS. 5 and 7, as well as the series represented by FIGS. 15 and 16. Alternatively, in another embodiment of sequential initiation, left pinion 84, third and fourth pins 88, 90, and/or third and fourth actuators 92, 96 may be configured such that actuation of distal fingers 38 does not begin until distal sheath 34 is fully extended. In yet another alternate embodiment of sequential initiation, actuation of distal fingers 38 is initiated before extension of distal sheath 34 is initiated. It will be appreciated that, in any of the foregoing embodiments, the delay may be effected even with a single, continuous (i.e., uninterrupted) motion of left actuator slider 28. Still other ways in which the delay may be achieved or embodied will be apparent to those of ordinary skill in the art. Alternatively, it will be appreciated that other configurations exist where a delay is not necessary or otherwise desirable.

Regardless of whether there is a delay between the initiation of distal sheath 34 extension and distal finger 38 actuation (e.g., delay experienced with sequential extension and actuation), those of ordinary skill in the art will appreciate that extension of distal sheath 34 and actuation of distal fingers 38 may be effected, at least in part, contemporaneously. In other words, at least a portion of the act of extending distal sheath 34 may be performed contemporaneously with at least a portion of the act of actuating distal fingers 38. Thus, as the term is used herein, "contemporaneously" should not be read to require that these two acts begin and/or end at the same time, although it would include a configuration where the two acts begin and/or end at the same time. "Contemporaneously" would include any configuration where there is at least some temporal overlap between the acts of extending distal sheath 34 and actuating distal fingers 38. "Partially contemporaneously" would include any configuration where the acts of extending distal sheath 34 and actuating distal fingers 38 have temporal overlap, but begin and/or end at different times. As used herein, the term "sequential" and its variants should be read to include configurations where the acts of extending distal sheath 34 and actuating distal fingers 38 begin and/or end at different times. Of course, applier 10 may be configured such that the acts may be performed both contemporaneously and sequentially with the same applier 10 (e.g., the acts begin at different times yet there is temporal overlap in their performance). Any of the foregoing results may be obtained with a single, continuous motion of left actuator slider 28. While such may be provided by the applier 10 of the present example, it will be appreciated that, in actual use, motion of left actuator slider 28 need not in fact be a single, continuous motion.

While handle 17 of the present example includes left and right actuator sliders 28, 26 in a side-by-side positioning, it will be appreciated that left and right actuator sliders 28, 26 need not be in such positioning. By way of example only, handle 17 may be configured such that left and right actuator sliders 28, 26 are aligned longitudinally. In another embodiment, retraction of proximal sheath 32, advancement of distal sheath 34, and/or actuation of deployment mechanism 24 is accomplished through distal movement of right and/or left actuator sliders 28, 26. It will also be appreciated that a variety of other features, configurations, or mechanisms may be used to supplement or substitute left and right actuator sliders 28, 26.

Figure 12:
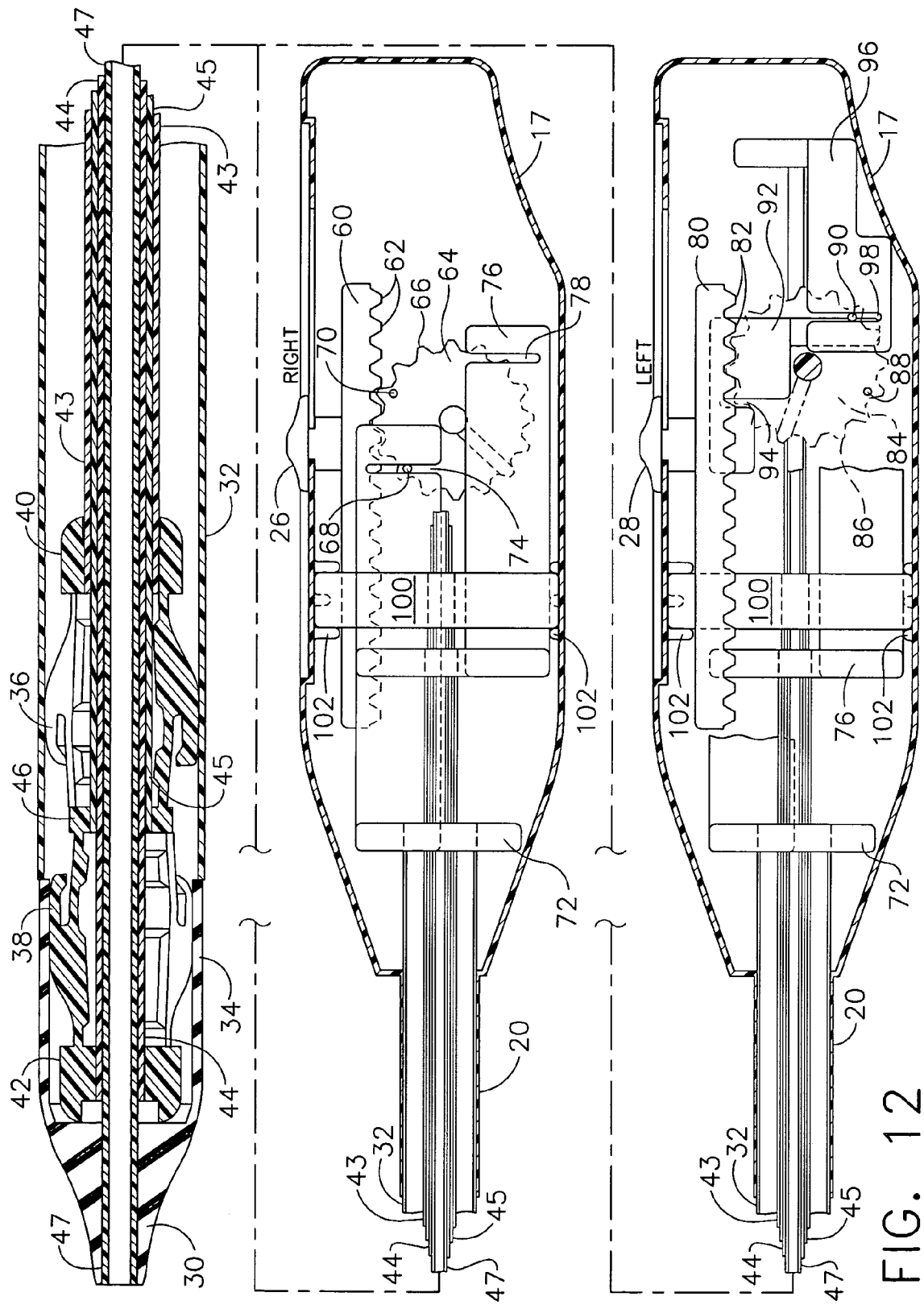
FIG. 12 is a partial cross-sectional view of the distal portion, a right handle portion, and a left handle portion of the device of FIG. 1.

In one example of operation, anastomotic ring 14 is held on ring deployment mechanism 24 by proximal and distal fingers 36, 38. Applier 10 is inserted adjacent the anastomosis site, where an opening is formed in two proximate gastrointestinal walls 200, 300. A suitable configuration of applier 10 for insertion is shown in FIGS. 1 and 12. As applier 10 is inserted, proximal and distal sheaths 32, 34 act to prevent tissue from becoming caught or trapped in ring deployment mechanism 24. Of course, any other suitable structure may be used to serve such a purpose. It will also be appreciated that, when included, sheaths 32, 34 may serve a variety of other purposes.

Figure 5:
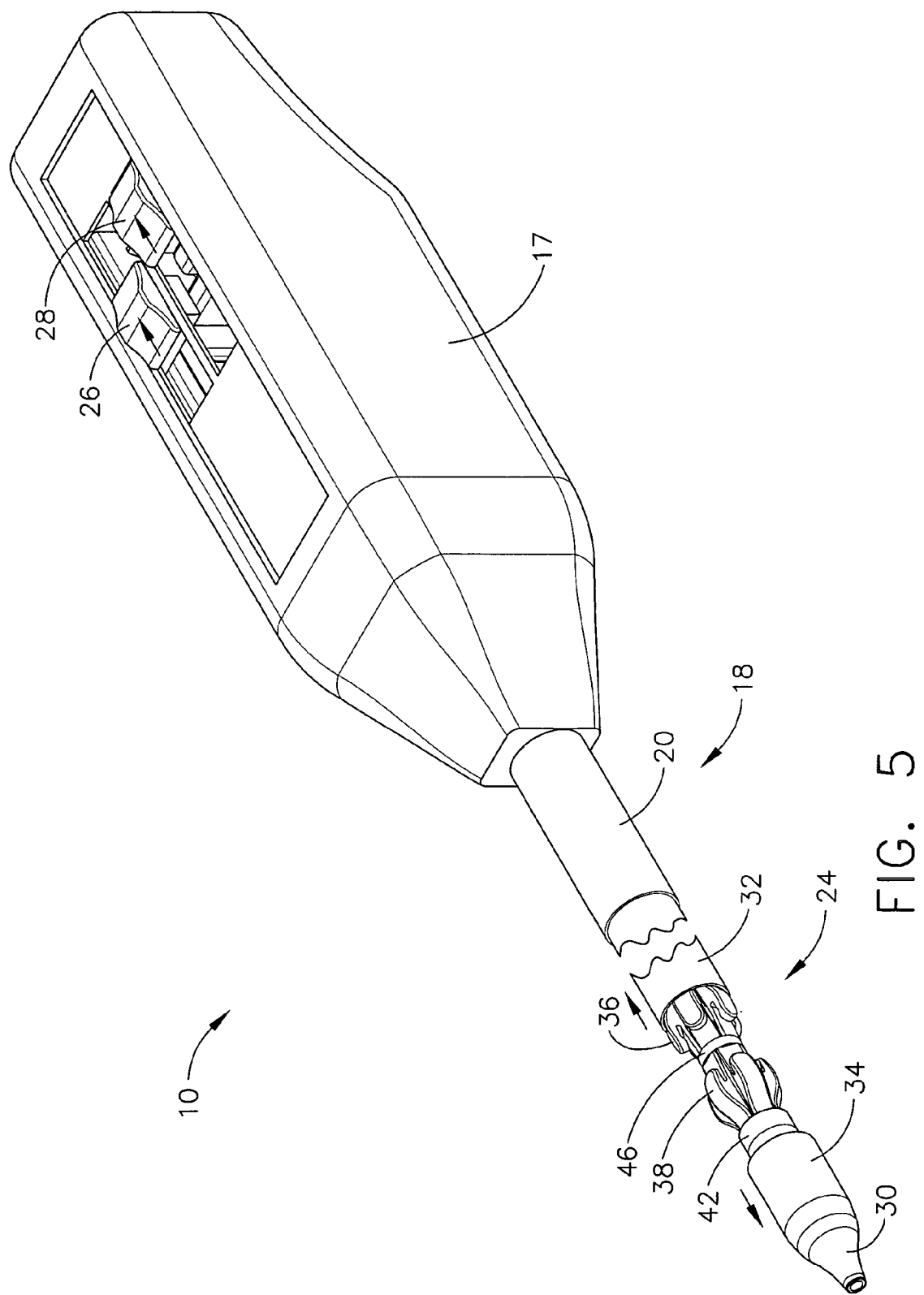
FIG. 5 is a perspective view of the anastomotic ring applier device of FIG. 1 with the distal sheath portion extended and the proximal sheath portion partially retracted.

Once ring deployment mechanism 24 is inserted into the anastomotic opening, right and left actuator sliders 26, 28 may be moved proximally, thereby revealing ring deployment mechanism 24 by retracting proximal sheath 32 proximally and advancing distal sheath 34 distally. This stage of use is shown in FIG. 5. Of course, each sheath 32, 34 may be retracted and advanced, respectively, individually instead of concomitantly, in any suitable order. Such individual retraction and advancement of sheaths 32, 34, respectively, is shown in FIGS. 13 and 15.

Figure 6:
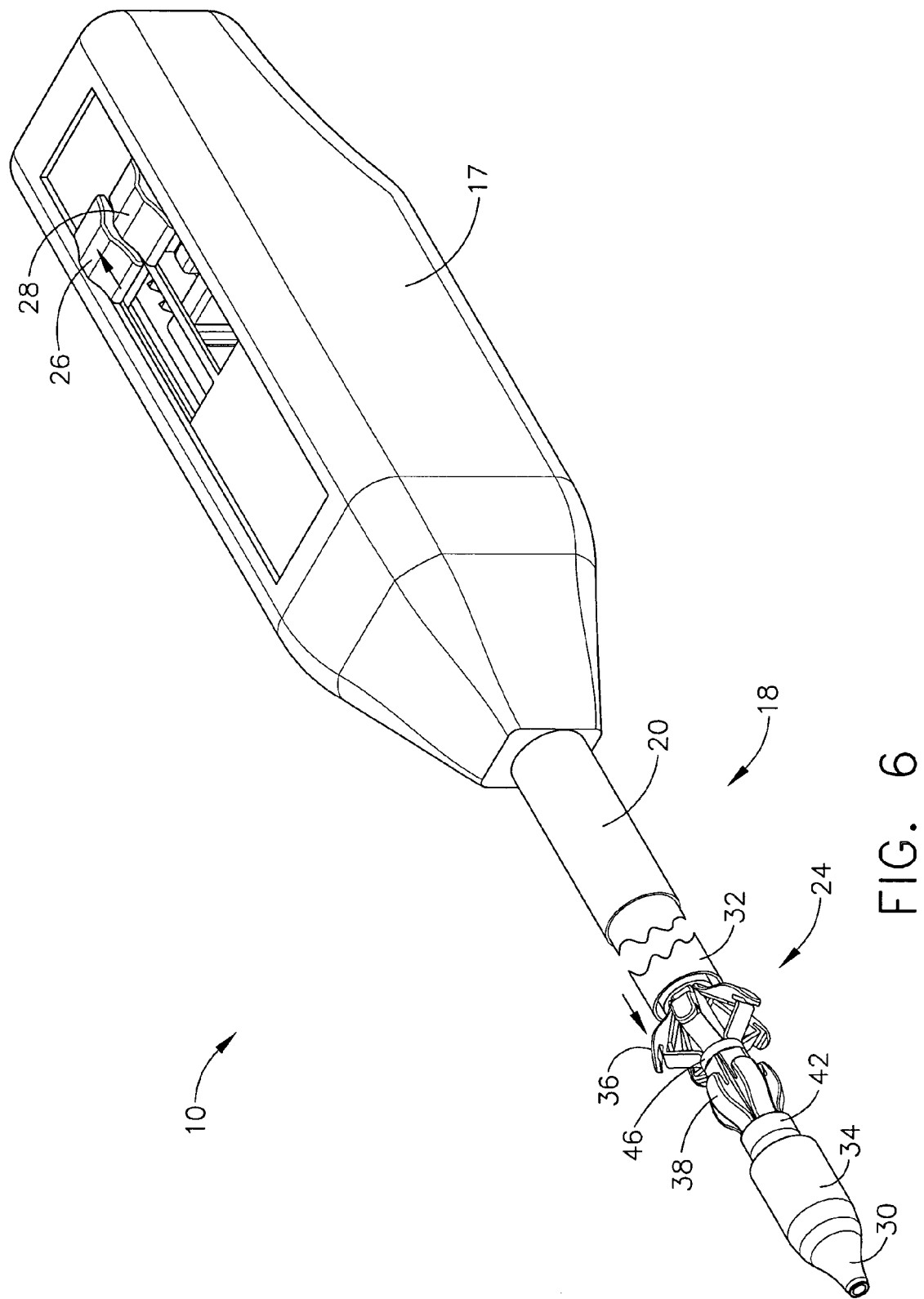
FIG. 6 is a perspective view of the device of FIG. 1 with the proximal sheath portion partially retracted and the proximal portion of the ring deployment mechanism partially actuated.
Figure 7:
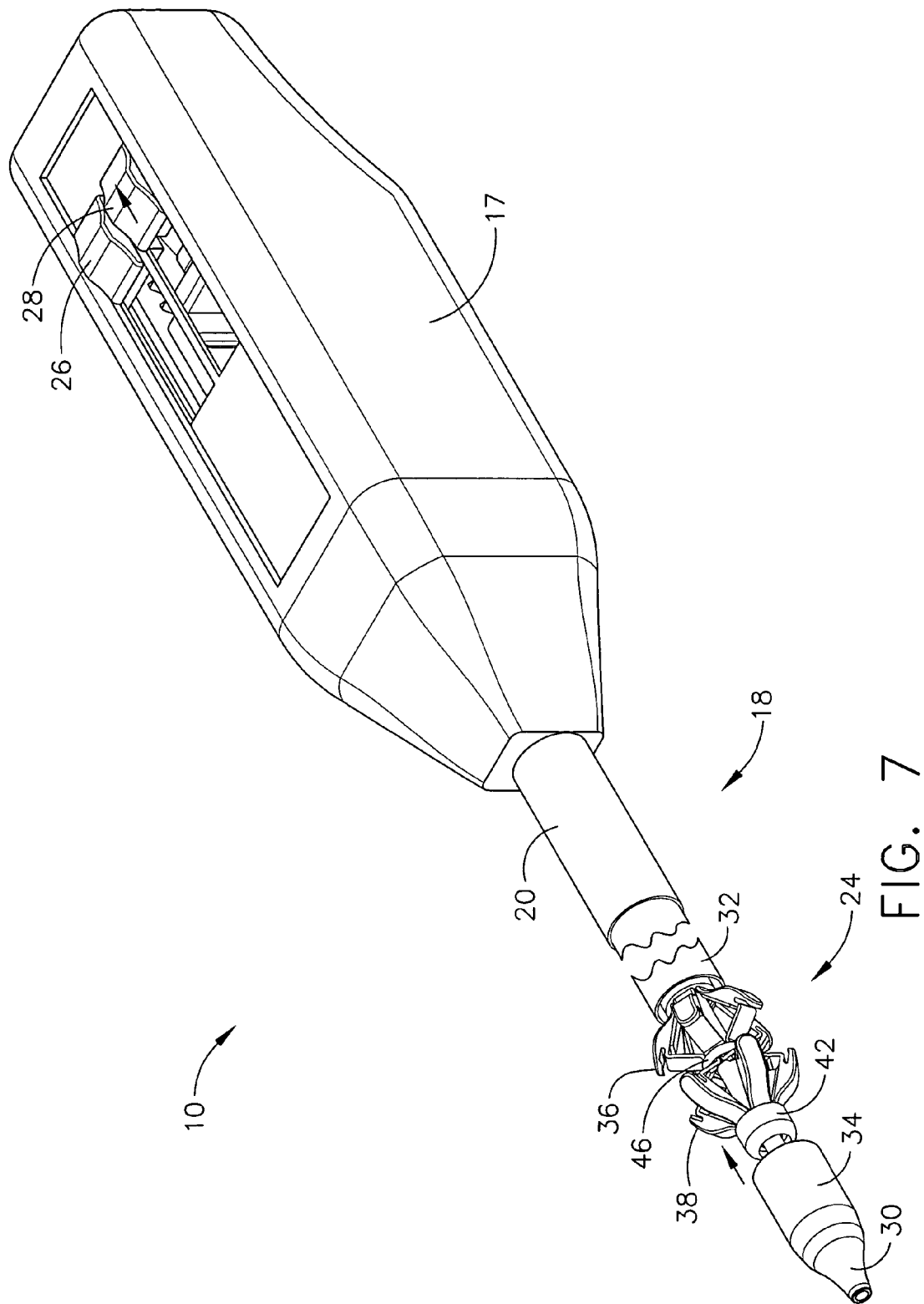
FIG. 7 is a perspective view of the device of FIG. 1 with the distal and proximal portions of the ring deployment mechanism partially actuated.
Figure 8:
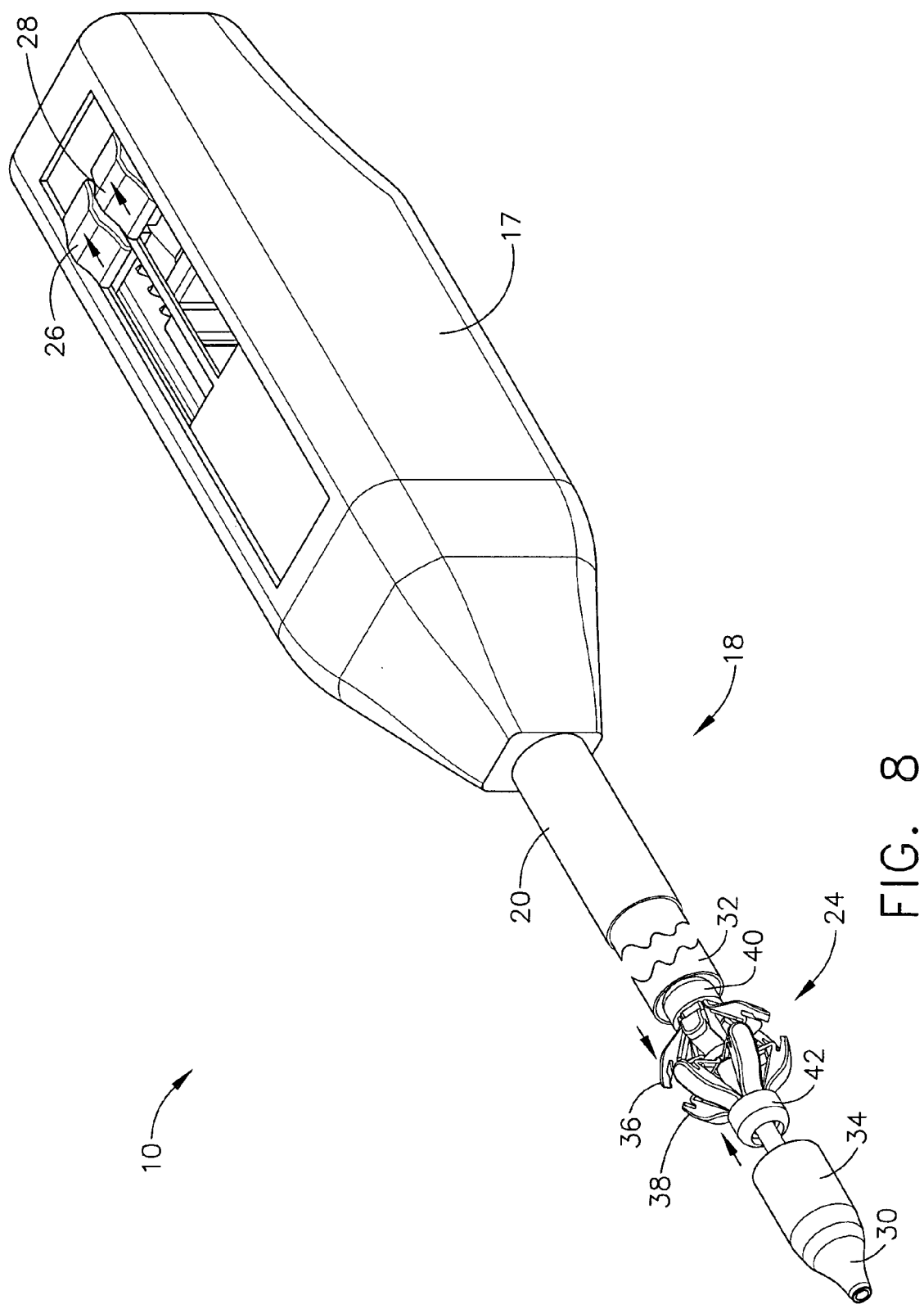
FIG. 8 is a perspective view of the device of FIG. 1 with the distal and proximal portions of the ring deployment mechanism fully actuated.
Figure 9:
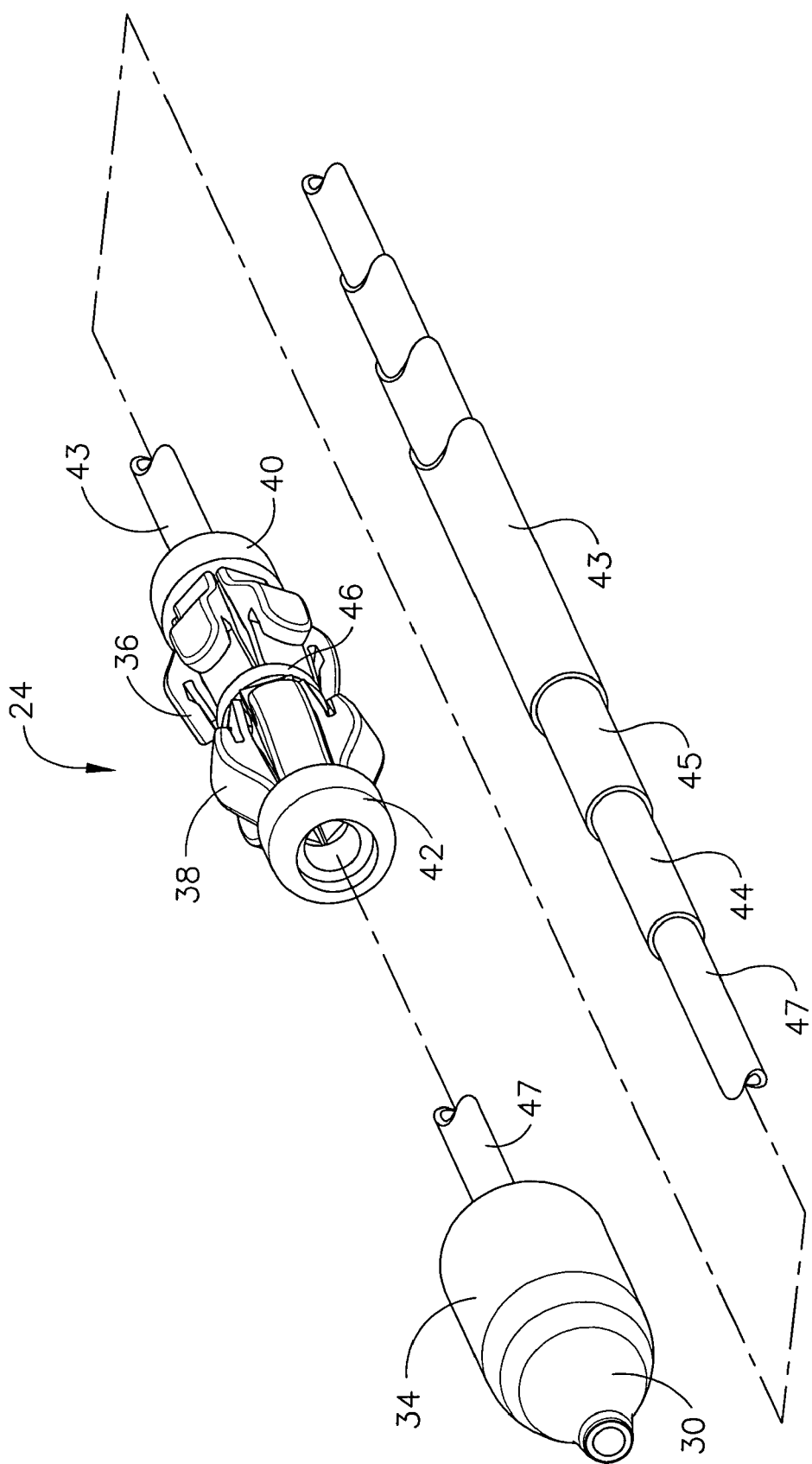
FIG. 9 is a perspective exploded view of the ring deployment mechanism of the device of FIG. 1.
Figure 10:
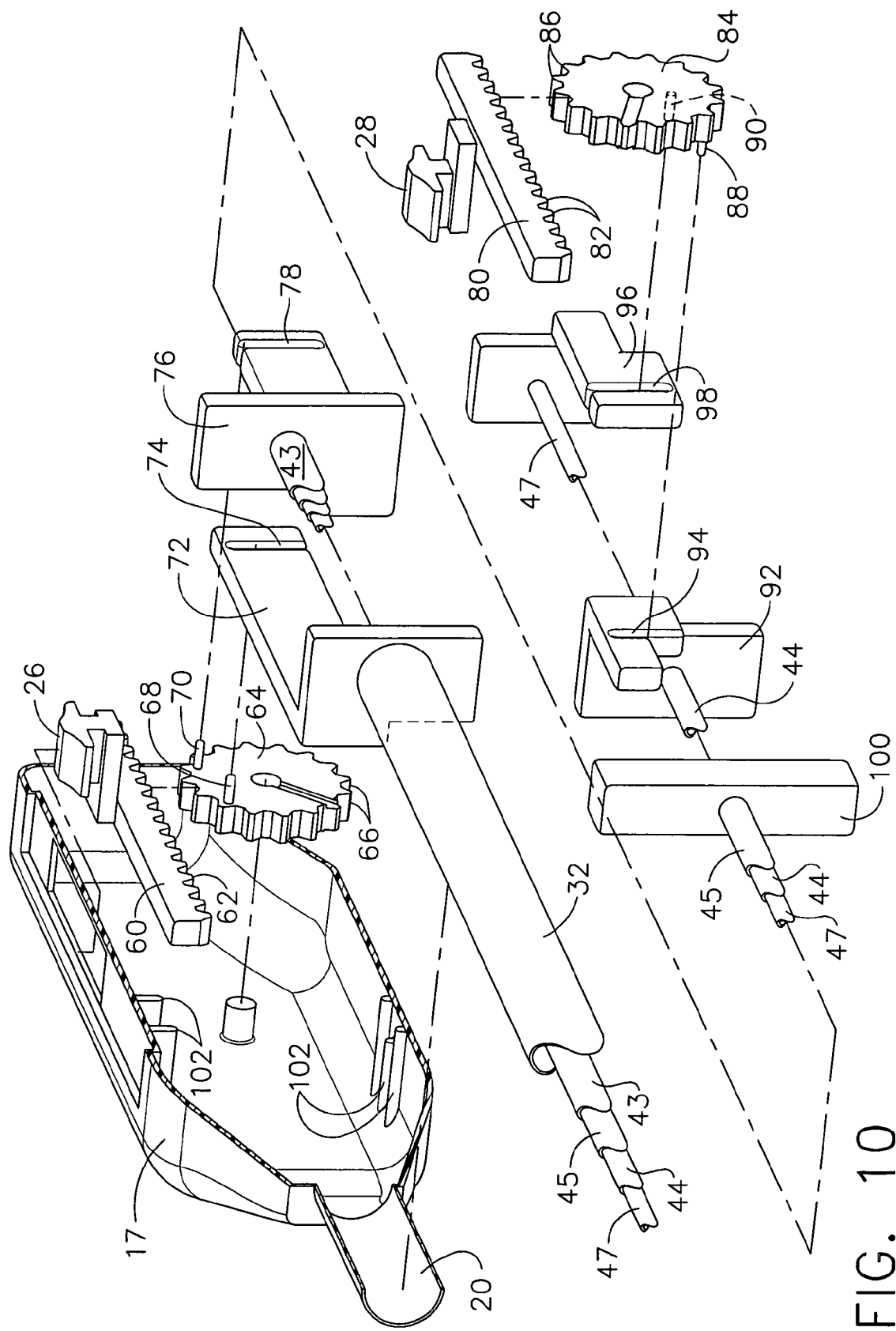
FIG. 10 is a perspective, cross-sectional exploded view of a proximal portion of the device of FIG. 1 with a left housing half omitted.
Figure 11:
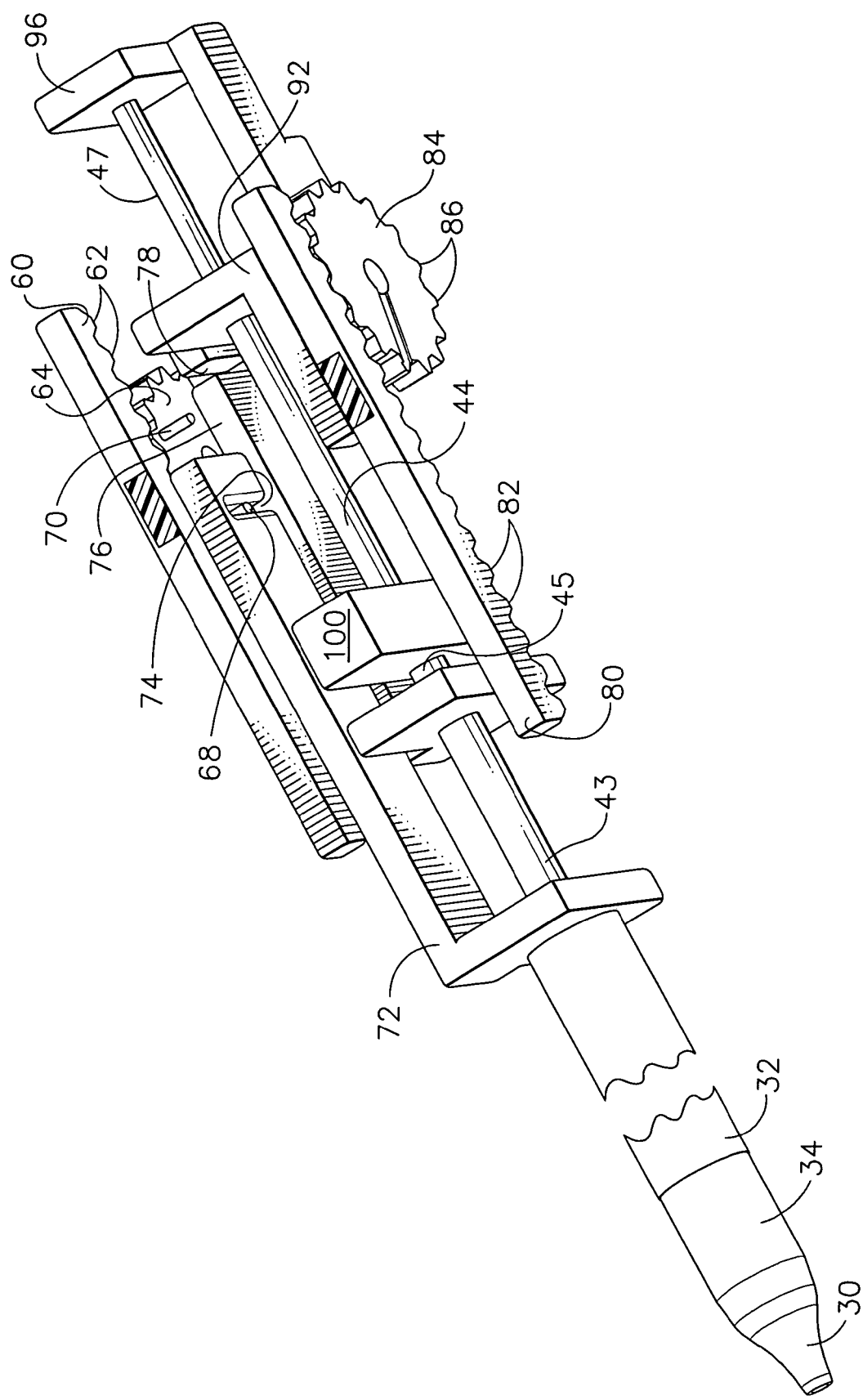
FIG. 11. is perspective exploded view of the actuation mechanism of the device of FIG. 1.
Figure 17:
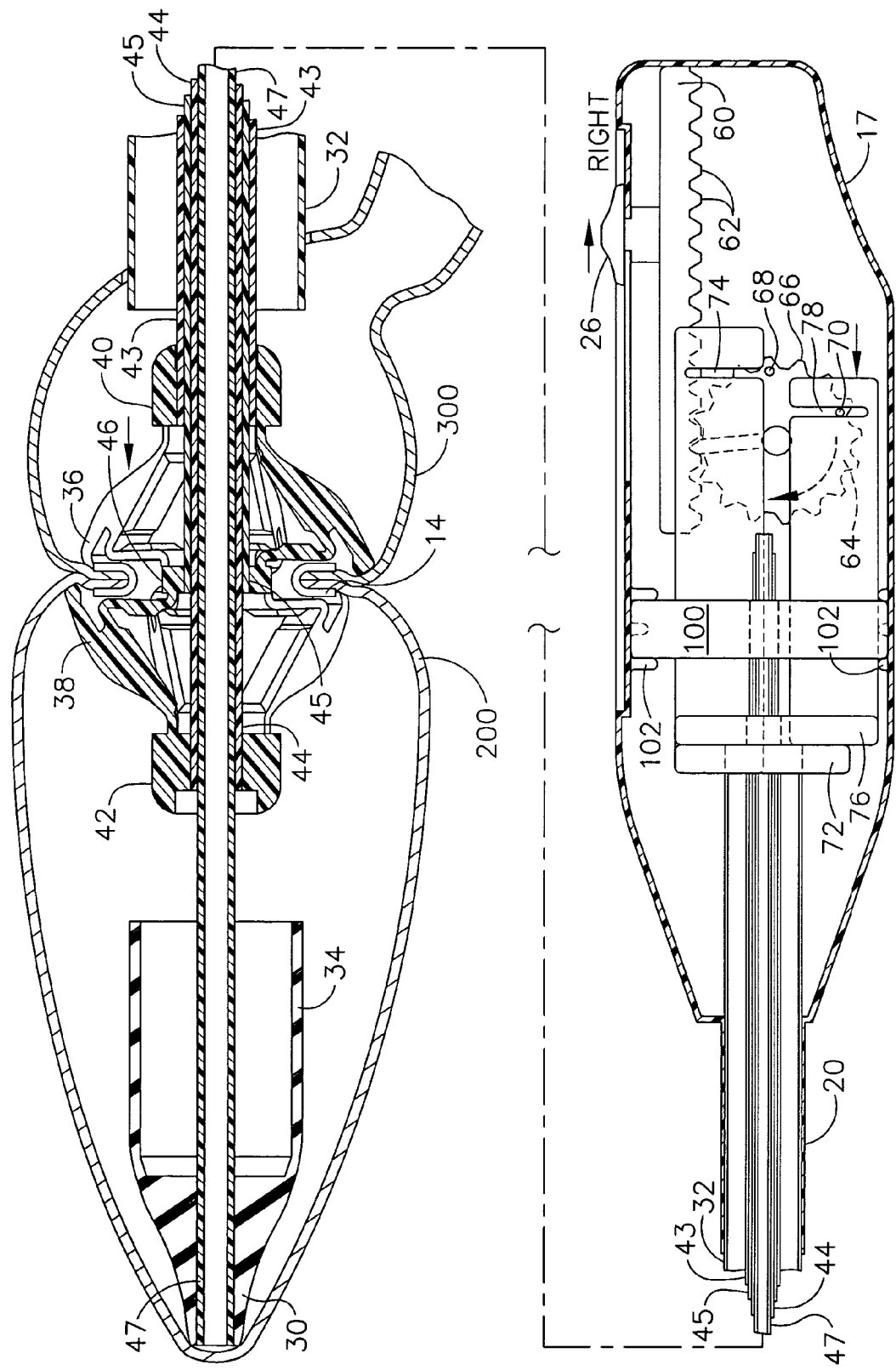
FIG. 17 is a partial cross-sectional view of the distal portion and the right handle portion of the device of FIG. 1, shown with the distal and proximal portions of the ring deployment mechanism fully actuated.
Figure 18:
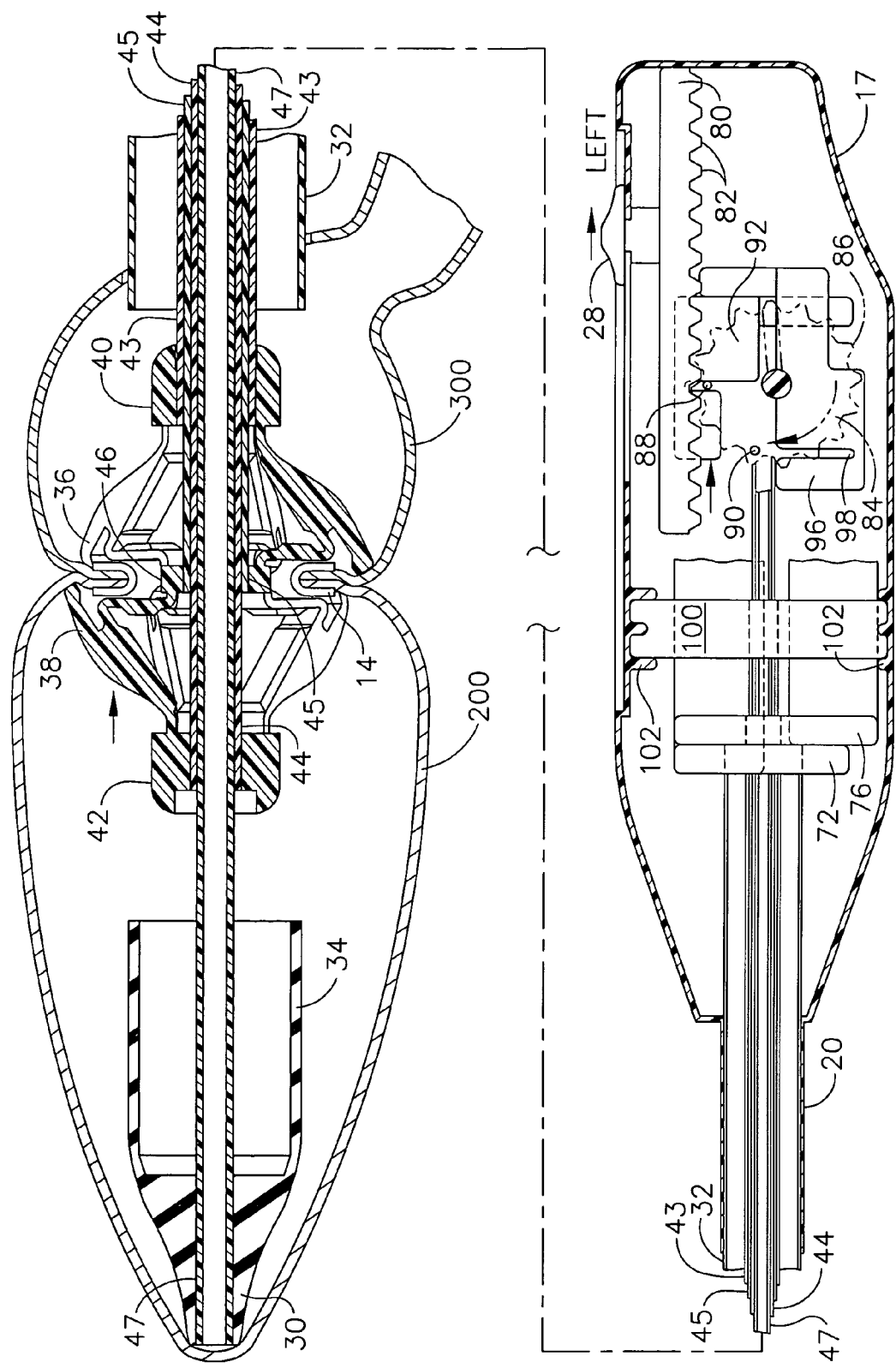
FIG. 18 is a partial cross-sectional view of the distal portion and the left handle portion of the device of FIG. 1, shown with the distal and proximal portions of the ring deployment mechanism fully actuated.
Figure 19:
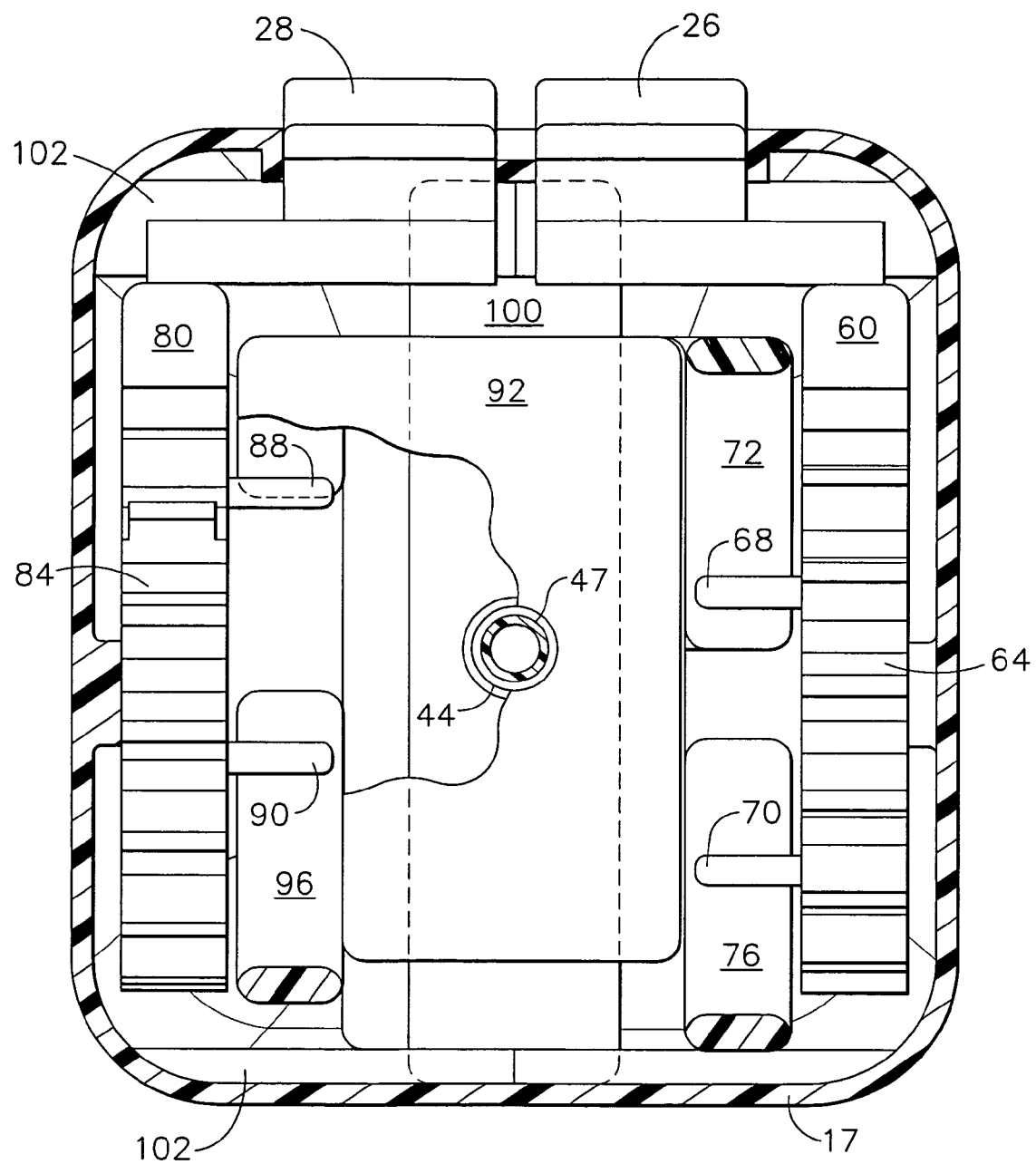
FIG. 19 is a cross-sectional view taken along Plane 19 of FIG. 14.
Figure 20:
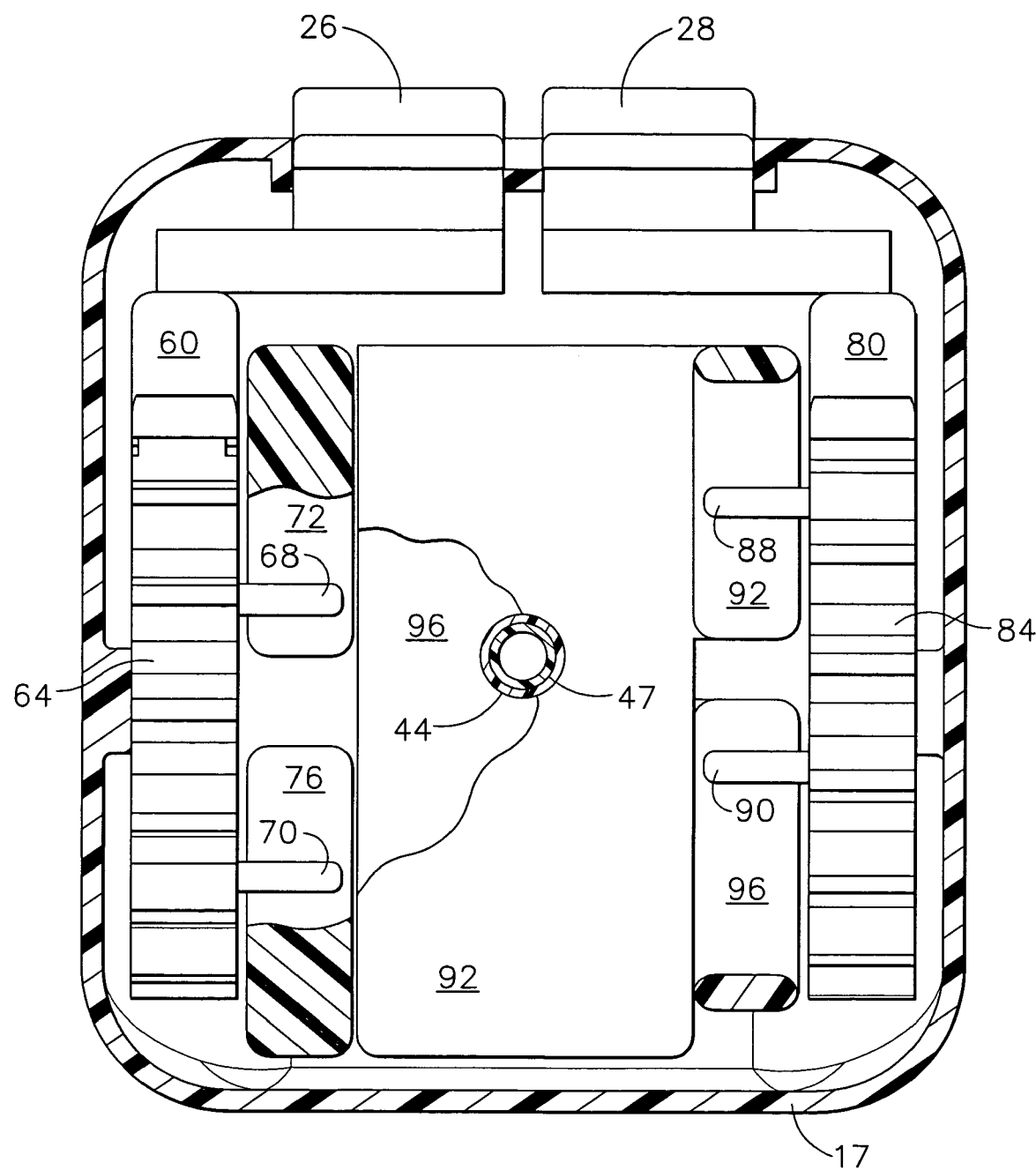
FIG. 20 is a cross-sectional view taken along Plane 20 of FIG. 15.

With ring deployment mechanism 24 having been at least partially revealed, continued proximal movement of right actuator slider 26 begins actuation of proximal fingers 36. FIGS. 6 and 14 show proximal fingers 36 in a partially actuated configuration. Similarly, continued proximal movement of left actuator slider 28 begins actuation of distal fingers 38. FIGS. 7 and 16 show distal fingers 38 in a partially actuated configuration. During this time, or at any other time during operation, the surgeon may check to ensure proper orientation and/or positioning of applier 10, such as with an endoscope, by way of example only. Assuming proper orientation and/or positioning of applier 10, proximal movement of right and left actuator sliders 26, 28 may continue to place proximal and distal fingers 36, 38 in a fully actuated position, respectively. This may expand anastomotic ring 14 (or allow anastomotic ring 14 to expand) from its compressed, cylindrical-shaped position to its actuated, hollow rivet-shaped position, forming an anastomotic attachment between gastrointestinal tissue walls 200, 300. Anastomotic ring 14 will thus be deployed. Fully actuated fingers 36, 38 are shown in FIGS. 8, 17, and 18.

Upon deployment of anastomotic ring 14, the foregoing steps may be reversed to de-actuate ring deployment mechanism 24, move distal sheath 34 proximally, and move proximal sheath 32 distally, such that applier 10 is again in a configuration similar to that shown in FIGS. 1 and 12. When applier 10 reaches such configuration, applier 10 may be withdrawn from the patient. During withdrawal, as during insertion, sheaths 32, 34 may prevent tissue from getting caught or trapped in ring deployment mechanism 24. Of course, any other suitable structure may be used to serve such a purpose.

Other applications and methods of operating applier 10 will be apparent to those of ordinary skill in the art.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings. Additional advantages may readily appear to those skilled in the art.

What is claimed is:

1. A surgical instrument for implanting an anastomotic ring device, comprising:
   (a) a ring deployment mechanism configured to receive an anastomotic ring, wherein the ring deployment mechanism is operable to move between an unactuated position and an actuated position;
   (b) a shaft in communication with the ring deployment mechanism, wherein the shaft comprises:
      (i) one or more transfer members operatively configured to transfer actuating forces to the ring deployment mechanism, and
      (ii) a sheath device operable to selectively move from a first configuration to a second configuration, wherein the sheath device is configured to cover at least a portion of the ring deployment mechanism when the sheath device is in the first configuration, wherein the sheath device is configured to uncover the at least a portion of the ring deployment mechanism when the sheath device is moved to the second configuration; and
   (c) an actuation mechanism operable to perform at least a portion of an act of actuating at least a portion of the ring deployment mechanism and at least a portion of an act of moving at least a portion of the sheath device to the second configuration contemporaneously wherein the actuation mechanism comprises:
      (i) a first actuator,
      (ii) a second actuator, (iii) a first member comprising a pinion having a face, an axis, and a pair of pins extending from the face in a direction parallel to the axis, wherein the first member is operable to communicate a first actuating force to the first actuator and a second actuating force to the second actuator, wherein the first actuating force is longitudinally opposed in direction relative the second actuating force;

wherein the first and second actuators each comprise a slot, wherein the pins are configured to engage the slots to communicate the first and second actuating forces substantially contemporaneously.

2. The surgical instrument of claim 1, wherein at least a portion of the actuation mechanism is located in a handle connected to the shaft.

3. The surgical instrument of claim 1, wherein the one or more transfer members comprise a plurality of tubes.

4. The surgical instrument of claim 1, wherein the actuation mechanism is further operable to initiate the act of moving at least a portion of the sheath device to the second configuration and initiate the act of actuating at least a portion of the ring deployment mechanism sequentially.

5. The surgical instrument of claim 1, wherein the ring deployment mechanism comprises a plurality of fingers.

6. The surgical instrument of claim 1, wherein the ring deployment mechanism comprises a proximal portion moveable from the unactuated position to the actuated position, and a distal portion moveable from the unactuated position to the actuated position.

7. The surgical instrument of claim 6, wherein the sheath device comprises a proximal sheath and a distal sheath, wherein the proximal sheath is in a third configuration when the sheath device is in the first configuration, wherein the proximal sheath is in a fourth configuration when the sheath device is in the second configuration, wherein the distal sheath is in a fifth configuration when the sheath device is in the first configuration, and wherein the distal sheath is in a sixth configuration when the sheath device is in the second configuration.

8. The surgical instrument of claim 7, wherein the proximal sheath is configured to cover the proximal portion of the ring deployment mechanism when the proximal sheath is in the third configuration, and wherein the distal sheath is configured to cover the distal portion of the ring deployment mechanism when the distal sheath is in the fifth configuration.

9. The surgical instrument of claim 8, wherein the actuation mechanism further comprises a first actuator slider operable to communicate motion to the proximal portion of the ring deployment mechanism, and a second actuator slider operable to communicate motion to the distal portion of the ring deployment mechanism.

10. The surgical instrument of claim 9, wherein the first actuator slider is further operable to move the proximal sheath from the third configuration to the fourth configuration.

11. The surgical instrument of claim 10, wherein the first actuator slider is operable to move the proximal portion of the ring deployment mechanism toward the actuated position and the proximal sheath toward the fourth configuration contemporaneously.

12. The surgical instrument of claim 11, wherein the second actuator slider is further operable to move the distal sheath from the fifth configuration to the sixth configuration.

13. The surgical instrument of claim 12, wherein the second actuator slider is operable to move the distal portion of the ring deployment mechanism toward the actuated position and the distal sheath toward the sixth configuration contemporaneously.

14. The surgical instrument of claim 1, wherein the sheath device is configured to move in one or two longitudinal directions from the first configuration to the second configuration.

15. The surgical instrument of claim 1, wherein the first actuator is in communication with at least a portion of the sheath device, and wherein the second actuator is in communication with at least a portion of the ring deployment mechanism.

16. The surgical instrument of claim 15, further comprising an actuator slider in communication with a rack, wherein the rack is in communication with the pinion.

* * * * *